US012325692B2

(12) United States Patent
Hernández Cabanillas et al.

(10) Patent No.: US 12,325,692 B2
(45) Date of Patent: Jun. 10, 2025

(54) USES OF DOXADIAZINES COMPOUNDS

(71) Applicant: HORITZONTS TECNOLOGICS HUNGARY KORLÁTOLT FELELOSSÉGU TÁRSASÁG, Budapest (HU)

(72) Inventors: Alfredo Hernández Cabanillas, Madrid (ES); Santiago Maderuelo Corral, Madrid (ES); Montserrat Ortega Doménech, Madrid (ES); Diego Fernando Rosero Valencia, Madrid (ES); Ángel Rumbero Sánchez, Madrid (ES); Victor Tena Pérez, Badajoz (ES); Luis Néstor Apaza Ticona, Madrid (ES)

(73) Assignee: HORITZONTS TECNOLOGICS HUNGARY KORLÁTOLT FELELOSSÉGU TÁRSASÁG, Budapest (HU)

( * ) Notice: Subject to any disclaimer, the term of this patent is extended or adjusted under 35 U.S.C. 154(b) by 791 days.

(21) Appl. No.: 17/595,877

(22) PCT Filed: Jun. 1, 2020

(86) PCT No.: PCT/EP2020/065116

§ 371 (c)(1),
(2) Date: Nov. 29, 2021

(87) PCT Pub. No.: WO2020/240037

PCT Pub. Date: Dec. 3, 2020

(65) Prior Publication Data

US 2022/0315544 A1 Oct. 6, 2022

(30) Foreign Application Priority Data

May 31, 2019 (EP) .................................... 19382449

(51) Int. Cl.

| | |
|---|---|
| ***C07D 273/04*** | (2006.01) |
| ***A23L 5/41*** | (2016.01) |
| ***A61K 8/49*** | (2006.01) |
| ***A61Q 19/02*** | (2006.01) |

(52) U.S. Cl.

CPC .............. *C07D 273/04* (2013.01); *A23L 5/41* (2016.08); *A61K 8/49* (2013.01); *A61Q 19/02* (2013.01); *A61K 2800/522* (2013.01)

(58) Field of Classification Search

None

See application file for complete search history.

(56) References Cited

U.S. PATENT DOCUMENTS 3,251,838 A 5/1966 Kalm
11,008,295 B2 * 5/2021 Hernández .............. A61P 31/22

FOREIGN PATENT DOCUMENTS

EP 3156400 A1 4/2017
EP 3395805 A1 10/2018

OTHER PUBLICATIONS

Alam et al., “Consequence of the antioxidant activities and tyrosinase inhibitory effects of various extracts from the fruiting bodies of Pleurotus ferulae”, Saudi Journal of Biological Sciences, vol. 19, pp. 111-118, 2012.

Alves Dos Santos et al., “HIF-1alpha and infectious diseases: a new frontier for the development of new therapies”, Rev Inst Med Trop São Paulo., vol. 59, e92, pp. 1-10, 2017.

Andrés et al., “NF-κB and STAT3 Inhibition as a Therapeutic Strategy in Psoriasis: In Vitro and In Vivo Effects of BTH”, Journal of Investigative Dermatology, vol. 133, pp. 1-11, 2013.

Baharav et al., “Tyrosinase as an autoantigen in patients with vitiligo”, Clin Exp Immunol, vol. 105, pp. 84-88, 1996.

Bashir et al, “TNF-α production in the skin”, Arch Dermatol Res., vol. 301, pp. 87-91, 2009.

Bony et al., “Stimulating Nrf2 and Inhibiting NF-κB to Help Skin Combating Pollution”, Sofwjournal, vol. 144, pp. 1-7, 2018.

Calautti et al., “Psoriasis: A STAT3-Centric View”, International Journal of Molecular Sciences, vol. 19, No. 171, pp. 1-14, 2018.

Cerychova et al., “Adverse effects of Hif1α mutation and maternal diabetes on the offspring heart”, Cardiovasc Diabetol, vol. 17, No. 68, pp. 1-17, 2018.

Chen et al., “A Novel Inhibitor Against Mushroom Tyrosinase with a Double Action Mode and Its Application in Controlling the Browning of Potato”, Food Bioprocess Technol., pp. 1-10, 2017.

Chiocchio et al., “Screening of a hundred plant extracts as tyrosinase and elastase inhibitors, two enzymatic targets of cosmetic interest”, Industrial Crops and Products, vol. 122, pp. 498-505, Oct. 15, 2018.

Correia et al., “Defective HIF Signaling Pathway and Brain Response to Hypoxia in Neurodegenerative Diseases: Not an “Iffy” Question!”, Current Pharmaceutical Design, vol. 19, pp. 1-15, 2013.

(Continued)

*Primary Examiner* — Brian J Davis

(74) *Attorney, Agent, or Firm* — McKee, Voorhees & Sease, PLC

(57) ABSTRACT

The present invention relates to a compound of formula (I) or a pharmaceutically acceptable salt, stereoisomer or solvate thereof for use in the prevention and/or treatment of a pathology associated with proinflammatory conditions, a disease associated with oxidative stress or production of reactive oxygen species or a skin pigmentation disorder. In addition, the invention also relates to a cosmetic method for preventing and/or treating skin aging, irradiated skin or for skin-whitening comprising administering a compound of formula (I) or a cosmetically acceptable salt, stereoisomer or solvate thereof. In addition, the invention relates to a method of inhibition of enzymatic browning in food or beverage comprising contacting said food or beverage with a compound of formula (I) or a salt, stereoisomer or solvate thereof under conditions sufficient to inhibit enzymatic browning of said food or beverage.

13 Claims, 8 Drawing Sheets

(56) References Cited

OTHER PUBLICATIONS

Eskandani et al., "Oxidative Stress Level and Tyrosinase Activity in Vitiligo Patients", Indian Journal of Dermatology, vol. 55, No. 1, pp. 15-19, 2010.

Garcia-Perez et al., "A New Strategy Based on Recombinant Viruses as a Tool for Assessing Drug Susceptibility of Human Immunodeficiency Virus Type 1", Journal of Medical Virology, vol. 79, pp. 127-137, 2007.

Hadgraft et al., Modified-Release Drug Delivery Technology, https://www.researchgate.net/publication/43518951, pp. 1-13, 2004.

Han et al., "TNF-α stimulates activation of pro-MMP2 in human skin through NF-κB mediated induction of MT1-MMP", J Cell Sci., vol. 114, (Pt 1), pp. 131-139, Jan. 2001.

Hernández et al., Skin Lesions and Treatment With Tumor Necrosis Factor Alpha Antagonists, Reumatol Clin., vol. 9, No. 1, pp. 53-61, 2013.

Hogerlinden et al., "Inhibition of Rel/Nuclear Factor-κB signaling in skin results in defective DNA damage-induced cell cycle arrest and Ha-ras- and p53-independent tumor development", Oncogene, vol. 21, pp. 4969-4977, 2002.

International Searching Authority in connection with PCT/EP2020/065116 filed Jun. 1, 2020, "International Search Report", 14 pages, mailed Oct. 16, 2020.

Jordan et al., "Melanocyte-Directed Enzyme Prodrug Therapy (MDEPT): Development of a Targeted Treatment for Malignant Melanoma", Bioorganic & Medicinal Chemistry, vol. 7, pp. 1775-1780, 1999.

Ke et al., "Synthesis and Biological Properties of Dihydro-Oxadiazine-Based Hetero-cyclic Derivatives", Mini-Reviews In Medicinal Chemistry, vol. 11, pp. 642-657, 2011.

Loizzo et al., "Natural and Synthetic Tyrosinase Inhibitors as Antibrowning Agents: An Update", Comprehensive Reviews in Food Science and Food Safety, vol. 11, pp. 378-398, 2012.

Mace et al., "Sustained expression of Hif-1α in the diabetic environment promotes angiogenesis and cutaneous wound repair", Wound Repair and Regeneration, vol. 15, pp. 1-11, 2007.

Machado et al., "Targeted Prodrug Design for the Treatment of Malignant Melanoma", Journal of Dermatology Research and Therapy, vol. 2, Issue 2, pp. 1-8, 2016.

Merelli et al, "Understanding the Role of Hypoxia Inducible Factor During Neurodegeneration for New Therapeutics Opportunities", Current Neuropharmacology, vol. 16, pp. 1-16, 2018.

Miyoshi et al., "Stat3 as a Therapeutic Target for the Treatment of Psoriasis: A Clinical Feasibility Study with STA-21, a Stat3 Inhibitor", Journal of Investigative Dermatology, vol. 131, pp. 1-11, 2011.

Pagani et al., "Skin Rejuvenation through HIF-1α Modulation", Plastic and Reconstructive Surgery, vol. 141, No. 4, pp. 600e-607e, 2018.

Peyssonnaux et al., "HIF-1α expression regulates the bactericidal capacity of phagocytes", The Journal of Clinical Investigation, vol. 115, No. 7, pp. 1806-1815, Jul. 2005.

Peyssonnaux et al., "Critical Role of HIF-1α in Keratinocyte Defense against Bacterial Infection", Journal of Investigative Dermatology, vol. 128, pp. 1-6, 2008.

Rezvani et al., "HIF-1α in Epidermis: Oxygen Sensing, Cutaneous Angiogenesis, Cancer, and Non-Cancer Disorders", Journal of Investigative Dermatology, vol. 131, pp. 1-14, Jun. 2011.

Sahin, S. Cengiz, "The potential of Arthrospira platensis extract as a tyrosinase inhibitor for pharmaceutical or cosmetic applications", South African Journal of Botany, vol. 119, pp. 236-243, 2018.

Sano et al., "Impact of Stat3 activation upon skin biology: A dichotomy of its role between homeostasis and diseases", Journal of Dermatological Science, vol. 50, pp. 1-14, 2008.

Song et al., "The role of tyrosinase in autoimmune vitiligo", Lancet, vol. 344, pp. 1-5, 1994.

Sun et al., "Antioxidant and Anti-tyrosinase Activities of Phenolic Extracts from Rape Bee Pollen and Inhibitory Melanogenesis by cAMP/MITF/TYR Pathway in B16 Mouse Melanoma Cells", Frontiers in Pharmacology, vol. 8, Article 104, pp. 1-9, Mar. 2017.

Tanaka et al., "Protecting Skin Photoaging by NF-κB Inhibitor", Current Drug Metabolism, vol. 11, pp. 1-6, 2010.

Thangarajah et al., "HIF-1α dysfunction in diabetes", Cell Cycle, vol. 9, No. 1, pp. 1-6, Jan. 1, 2010.

Thibane et al., "The cosmetic potential of plants from the Eastern Cape Province traditionally used for skincare and beauty", South African Journal of Botany, vol. 122, pp. 475-483, 2019.

Vargas et al., "Exploiting Tyrosinase Expression and Activity in Melanocytic Tumors: Quercetin and the Central Role of p53", Integrative Cancer Therapies, pp. 1-15, 2010.

Wu et al., "Evaluation of Tyrosinase Inhibitory, Antioxidant, Antimicrobial, and Antiaging Activities of Magnolia officinalis Extracts after Aspergillus niger Fermentation", BioMed Research International, vol. 2018, Article ID 5201786, pp. 1-12, 2018.

Zaidi et al., "Microbial Tyrosinases: Promising Enzymes for Pharmaceutical, Food Bioprocessing, and Environmental Industry", Biochemistry Research International, vol. 2014, Article ID 854687, pp. 1-16, 2014.

Zhang et al., "Hypoxia Inducible Factor-1 as a Target for Neurodegenerative Diseases", Curr Med Chem., vol. 18, No. 28, pp. 1-21, Oct. 1, 2011.

Akash MS, Rehman K, Liaqat A. Tumor necrosis factor-alpha: role in development of insulin resistance and pathogenesis of type 2 diabetes mellitus. Journal of cellular biochemistry. Jan. 2018; 119(1):105-10.

Arjamaa O, Nikinmaa M, Salminen A, Kaarniranta K. Regulatory role of HIF-1α in the pathogenesis of age-related macular degeneration (AMD). Ageing research reviews. Oct. 1, 2009;8(4):349-58.

Barichello T, dos Santos I, Savi GD, Simões LR, Silvestre T, Comim CM, Sachs D, Teixeira MM, Teixeira AL, Quevedo J. TNF-α, IL-1β, IL-6, and cinc-1 levels in rat brain after meningitis induced by *Streptococcus pneumoniae*. Journal of neuroimmunology. Apr. 15, 2010;221(1-2):42-5.

Biddlestone J, Bandarra D, Rocha S. The role of hypoxia in inflammatory disease. International journal of molecular medicine. Apr. 1, 2015;35(4):859-69.

Duan RS, Wang HB, Yang JS, Scallon B, Link H, Xiao BG. Anti-TNF-α antibodies suppress the development of experimental autoimmune myasthenia gravis. Journal of autoimmunity. Dec. 1, 2002; 19(4):169-74.

Fernández-Torres J, Martínez-Nava GA, Gutiérrez-Ruíz MC, Gómez-Quiroz LE, Gutiérrez M. Role of HIF-1α signaling pathway in osteoarthritis: a systematic review. Revista brasileira de reumatologia. 2017;57(2):162-73.

Gao L, Chen Q, Zhou X, Fan L. The role of hypoxia-inducible factor 1 in atherosclerosis. Journal of clinical pathology. Oct. 1, 2012;65(10):872-6.

Gavino AC, Nahmod K, Bharadwaj U, Makedonas G, Tweardy DJ. STAT3 inhibition prevents lung inflammation, remodeling, and accumulation of Th2 and Th17 cells in a murine asthma model. Allergy. Dec. 2016;71(12):1684-92.

Jia H, Cui J, Jia X, Zhao J, Feng Y, Zhao P, Zang D, Yu J, Zhao T, Wang H, Xu K. Therapeutic effects of STAT3 inhibition by nifuroxazide on murine acute graft graft-vs.-host disease: old drug, new use. Molecular Medicine Reports. Dec. 1, 2017;16(6):9480-6.

Levin MC, Douglas JN, Meyers L, Lee S, Shin Y, Gardner LA. Neurodegeneration in multiple sclerosis involves multiple pathogenic mechanisms. Degenerative Neurological and Neuromuscular Disease. Mar. 12, 2014:49-63.

Liu SF, Malik AB. NF-κB activation as a pathological mechanism of septic shock and inflammation. American Journal of Physiology-Lung Cellular and Molecular Physiology. Apr. 2006;290(4):L622-45.

Madureira DF, Lima IL, Costa GC, Lages EM, Martins CC, Da Silva TA. Tumor necrosis factor-alpha in gingival crevicular fluid as a diagnostic marker for periodontal diseases: a systematic review. Journal of Evidence Based Dental Practice. Dec. 1, 2018;18(4):315-31.

Slight-Webb S, Guthridge JM, Chakravarty EF, Chen H, Lu R, Macwana S, Bean K, Maecker HT, Utz PJ, James JA. Mycophenolate mofetil reduces STAT3 phosphorylation in systemic lupus erythematosus patients. JCI insight. Jan. 1, 2019;4(2).

(56) References Cited

OTHER PUBLICATIONS

Tweedie D, Sambamurti K, Greig NH. TNF-α inhibition as a treatment strategy for neurodegenerative disorders: new drug candidates and targets. Current Alzheimer Research. Sep. 1, 2007;4(4):378-85.

Webb K, Tung R, Winterfield L, Gottlieb AB, Eby JM, Henning SW, Le Poole IC. Tumour necrosis factor-α inhibition can stabilize disease in progressive vitiligo. British Journal of Dermatology. Sep. 1, 2015;173(3):641-50.

* cited by examiner

USES OF DOXADIAZINES COMPOUNDS

TECHNICAL FIELD OF INVENTION

The present invention relates to the use of compounds of formula (I) for preventing and/or treating a pathology associated with proinflammatory conditions, a disease associated with oxidative stress or production of reactive oxygen species or a skin pigmentation disorder. The invention also relates to a cosmetic method and to a method for inhibition of enzymatic browning in food or beverage.

BACKGROUND OF INVENTION

Inflammation is a complex biological response to pathogens, cell damage, and biological irritants that may help an organism to remove injurious stimuli, and initiate the healing process for the tissue. There are two major categories of anti-inflammatory medicines: steroidal and non-steroidal. Steroidal anti-inflammatory medicines are based on hormonal substances, such as cortisone. Steroidal medications have a stronger anti-inflammatory response than non-steroidal medicines. Non-steroidal anti-inflammatory drugs have three major actions, all of which are related to inhibition of cyclo-oxygenase resulting in decreased formation of prostanoids. There are side effects to both of these groups of medicines that include stomach upset, stomach bleeding, or ulcers, kidney problems, hearing problems and ankle swelling.

Thus, although several methodologies are available for the treatment of such inflammatory diseases and diseases associated with oxidative stress or production of reactive oxygen species the results, however, are generally unsatisfactory as evidenced by a lack of efficacy and drug related side effects associated therewith.

Therefore, there is a need in the art of new compounds for treating pro-inflammatory disorders.

SUMMARY OF THE INVENTION

The inventors have observed that the compounds of formula (I) acts as anti-inflammatory and antioxidants compounds by inhibiting TNF-α activity, NF-ηB, STAT3, HIF-1α and tyrosinase activities.

In a first aspect, the invention relates to a compound of formula (I)

(I)

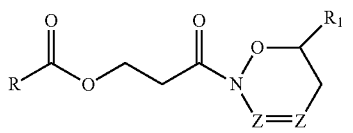

or a pharmaceutically acceptable salt, stereoisomer or solvate thereof, wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)$OCH_2$—, amine di-substituted with $C_{1-6}$ alkyl groups independently selected, b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)$R_3$—, —C(O)NH—$R_3$, —OC(O)$R_3$, and —C(O)$OR_3$—, wherein $R_3$ is $C_{1-6}$ alkyl, c) 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl, phenyl as defined in b), 5-6 membered aromatic ring group, halogen, ($C_{1-6}$ alkyl)$OCH_2$—, $C_{1-6}$alkoxy, amino di-substituted with $C_{1-6}$ alkyl groups, NHC(O)$R_3$—, —C(O)NH—$R_3$, —OC(O)$R_3$, and —C(O)$OR_3$—, wherein $R_3$ is $C_{1-6}$ alkyl d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from $C_{1-8}$alkyl, linear or branched $C_{2-8}$ alkenyl, $C_{5-6}$ cycloalkyl, phenyl as defined in b), 5-6 membered aromatic ring group, halogen, ($C_{1-6}$alkyl)$OCH_2$—, $C_{1-6}$ alkoxy, amino di-substituted with $C_{1-6}$alkyl groups, NHC(O)$R_3$—, —C(O)NH—$R_3$, —OC(O)$R_3$, and —C(O)$OR_3$—, wherein $R_3$ is $C_{1-6}$ alkyl, and e) —CH($R_4$)—CH($R_5$)COOH, wherein $R_4$ is selected from H, $NH_2$, OH and $CH_2COOH$, and wherein $R_5$ is selected from H, $NH_2$, OH and $CH_2COOH$ for use in the prevention and/or treatment of a pathology associated with proinflammatory conditions, a disease associated with oxidative stress or production of reactive oxygen species or a skin pigmentation disorder.

In a second aspect, the invention relates to a cosmetic method for preventing and/or treating skin aging, irradiated skin or for skin-whitening comprising administering a compound of formula (I)

(I)

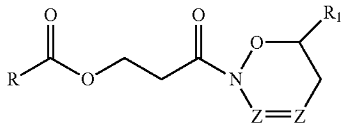

or a pharmaceutically acceptable salt, stereoisomer or solvate thereof, wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)$OCH_2$—, amine di-substituted with $C_{1-6}$ alkyl groups independently selected, b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)

$R_3$—, —C(O)NH—$R_3$, —OC(O)$R_3$, and —C(O)O$R_3$—, wherein $R_3$ is $C_{1-6}$ alkyl, c) 5-6 membered aromatic ring having one or more heteroatoms selected from N, S, and O and being optionally substituted with one or more groups independently selected from:
 $C_{1-8}$alkyl, linear or branched $C_{2-8}$ alkenyl, $C_{5-6}$ cycloalkyl,
 phenyl as defined in b),
 5-6 membered aromatic ring group,
 halogen,
 ($C_{1-6}$alkyl)O$CH_2$—, $C_{1-6}$ alkoxy,
 amino di-substituted with $C_{1-6}$ alkyl groups,
 NHC(O)$R_3$—, —C(O)NH—$R_3$, —OC(O)$R_3$, and —C(O)O$R_3$—, wherein $R_3$ is $C_{1-6}$ alkyl d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from
 $C_{1-5}$ alkyl, linear or branched $C_{2-8}$ alkenyl, $C_{5-6}$ cycloalkyl,
 phenyl as defined in b),
 5-6 membered aromatic ring group,
 halogen,
 ($C_{1-6}$alkyl)O$CH_2$—, $C_{1-6}$ alkoxy,
 amino di-substituted with $C_{1-6}$ alkyl groups,
 NHC(O)$R_3$—, —C(O)NH—$R_3$, —OC(O)$R_3$, and —C(O)O$R_3$—, wherein $R_3$ is $C_{1-6}$ alkyl, and e) —CH($R_4$)—CH($R_6$)COOH, wherein $R_4$ is selected from H, $NH_2$, H and $CH_2$COOH, and wherein $R_5$ is selected from H, $NH_2$, OH and $CH_2$COOH, to a subject in need thereof.

In a third aspect, the invention relates to a method of inhibition of enzymatic browning in food or beverage comprising contacting said food or beverage with a compound of formula (I) or a salt, stereoisomer or solvate thereof (I)

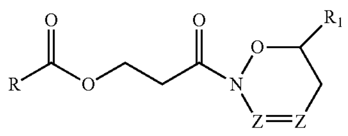

wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)O$CH_2$—, amine di-substituted with $C_{1-6}$ alkyl groups independently selected, b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)$R_3$—, —C(O)NH—$R_3$, —OC(O)$R_3$, and —C(O)O$R_3$—, wherein $R_3$ is $C_{1-6}$ alkyl, c) 5-6 membered aromatic ring having one or more heteroatoms selected from N, S, and O and being optionally substituted with one or more groups independently selected from:
 $C_{1-8}$ alkyl, linear or branched $C_{2-8}$ alkenyl, $C_{5-6}$ cycloalkyl,
 phenyl as defined in b),
 5-6 membered aromatic ring group,
 halogen,
 ($C_{1-6}$alkyl)O$CH_2$—, $C_{1-6}$ alkoxy,
 amino di-substituted with $C_{1-6}$ alkyl groups,
 NHC(O)$R_3$—, —C(O)NH—$R_3$, —OC(O)$R_3$, and —C(O)O$R_3$—, wherein $R_3$ is $C_{1-6}$ alkyl d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from
 $C_{1-8}$ alkyl, linear or branched $C_{2-8}$ alkenyl, $C_{5-6}$ cycloalkyl,
 phenyl as defined in b),
 5-6 membered aromatic ring group,
 halogen,
 ($C_{1-6}$alkyl)O$CH_2$—, $C_{1-6}$ alkoxy,
 amino di-substituted with $C_{1-6}$ alkyl groups,
 NHC(O)$R_3$, —C(O)NH—$R_3$, —OC(O)$R_3$, and —C(O)O$R_3$, wherein $R_3$ is $C_{1-6}$ alkyl, and e) —CH($R_4$)—CH($R_5$)COOH, wherein $R_4$ is selected from H, $NH_2$, OH and $CH_2$COOH, and wherein $R_5$ is selected from H, $NH_2$, OH and $CH_2$COOH, under conditions sufficient to inhibit enzymatic browning of said food or beverage.

Figure 1:
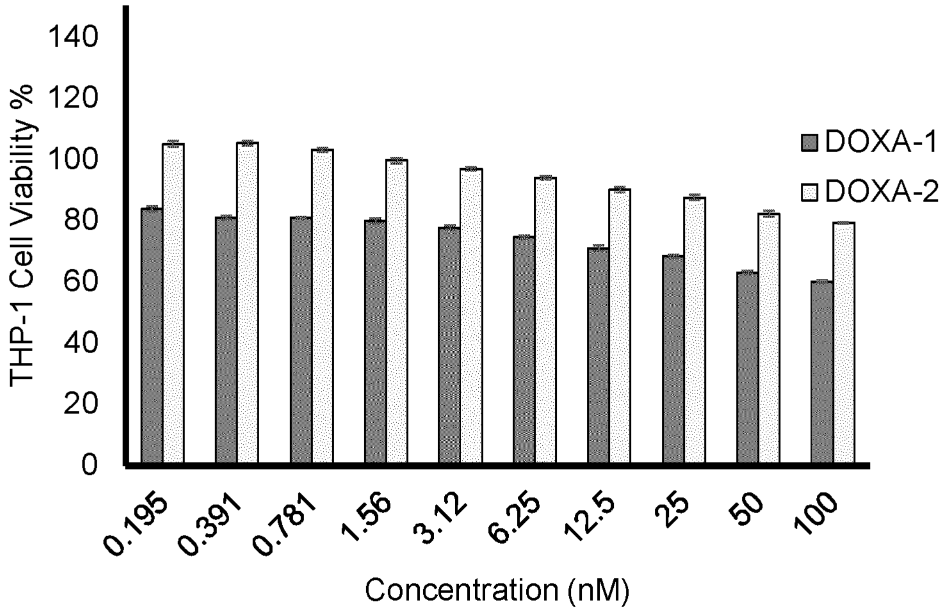
FIG. 1. Cytotoxic activities of the compound in THP-1 cells. The cells were treated with the test substance at the indicated concentrations for 48 h.

C. during 2 h and the activity was measured at 485 nm. Results are represented as percentage relative to untreated cells (control).

DETAILED DESCRIPTION OF THE INVENTION

Medical Uses

The inventors have observed that the compounds of formula (I) reduces pro-inflammatory conditions by inhibiting TNF-α activity, NF-ηB, STAT3, HIF-1α and tyrosinase activities. Therefore, the compounds of formula (I) are suitable for treating pathologies associated with proinflammatory conditions, with oxidative stress or production of reactive oxygen species or for treating skin pigmentation disorders.

Thus, in a first aspect, the invention relates to a compound of formula (I)

(I)

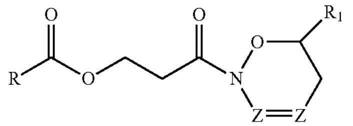

or a pharmaceutically acceptable salt, stereoisomer or solvate thereof, wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)$OCH_2$—, amine di-substituted with $C_{1-6}$ alkyl groups independently selected, b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)$R_3$—, —C(O)NH—$R_3$, —OC(O)$R_3$, and —C(O)$OR_3$—, wherein $R_3$ is $C_{1-6}$ alkyl, c) 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl, phenyl as defined in b), 5-6 membered aromatic ring group, halogen, ($C_{1-6}$alky)$OCH_2$—, $C_{1-6}$alkoxy, amino di-substituted with $C_{1-6}$ alkyl groups, NHC(O)$R_3$—, —C(O)NH—$R_3$, —OC(O)$R_3$, and —C(O)$OR_3$—, wherein $R_3$ is $C_{1-6}$ alkyl d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from $C_{1-8}$ alkyl, linear or branched $C_{2-8}$ alkenyl, $C_{5-6}$ cycloalkyl, phenyl as defined in b), 5-6 membered aromatic ring group, halogen, ($C_{1-6}$alkyl)$OCH_2$—, $C_{1-6}$alkoxy, amino di-substituted with $C_{1-6}$ alkyl groups, NHC(O)$R_3$—, —C(O)NH—$R_3$, —OC(O)$R_3$, and —C(O)$OR_3$—, wherein $R_3$ is $C_{1-6}$ alkyl, and e) —CH($R_4$)—CH($R_5$)COOH, wherein $R_4$ is selected from H, $NH_2$, OH and $CH_2COOH$, and wherein $R_5$ is selected from H, $NH_2$, OH and $CH_2COOH$ for use in the prevention and/or treatment of a pathology associated with proinflammatory conditions, a disease associated with oxidative stress or production of reactive oxygen species or a skin pigmentation disorder.

Alternatively, the invention relates to a method for preventing and/or treating a pathology associated with proinflammatory conditions, a disease associated with oxidative stress or production of reactive oxygen species or a skin pigmentation disorder comprising administering to a subject in need thereof a compound of formula (I)

(I)

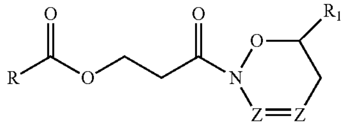

or a pharmaceutically acceptable salt, stereoisomer or solvate thereof, wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)$OCH_2$—, amine di-substituted with $C_{1-6}$ alkyl groups independently selected, b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)$R_3$—, —C(O)NH—$R_3$, —OC(O)$R_3$, and —C(O)$OR_3$—, wherein $R_3$ is $C_{1-6}$ alkyl, c) 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl, phenyl as defined in b), 5-6 membered aromatic ring group, halogen, ($C_{1-6}$alkyl)$OCH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)$OR_3$—, wherein $R_3$ is $C_{1-6}$ alkyl d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from $C_{1-8}$ alkyl, linear or branched $C_{2-8}$ alkenyl, $C_{5-6}$ cycloalkyl, phenyl as defined in b), 5-6 membered aromatic ring group, halogen, ($C_{1-6}$alkyl)$OCH_2$—, $C_{1-6}$ alkoxy, amino di-substituted with $C_{1-6}$ alkyl groups, $NHC(O)R_3$, $—C(O)NH—R_3$, $—OC(O)R_3$, and $—C(O)OR_3$, wherein $R_3$ is $C_{1-6}$ alkyl, and e) $—CH(R_4)—CH(R_5)COOH$, wherein $R_4$ is selected from H, $NH_2$, OH and $CH_2COOH$, and wherein $R_5$ is selected from H, $NH_2$, OH and $CH_2COOH$.

Alternatively, the invention relates to the use of a compound of formula (I)

(I)

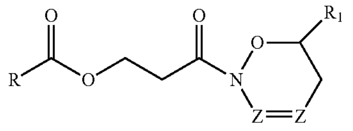

or a pharmaceutically acceptable salt, stereoisomer or solvate thereof, wherein one Z is N and the other is $—C—R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, $(C_{1-6}$ alkyl$)OCH_2—$, amine di-substituted with $C_{1-6}$ alkyl groups independently selected, b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, $—NHC(O)R_3—$, $—C(O)NH—R_3$, $—OC(O)R_3$, and $—C(O)OR_3—$, wherein $R_3$ is $C_{1-6}$ alkyl, c) 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl, phenyl as defined in b), 5-6 membered aromatic ring group, halogen, $(C_{1-6}$alkyl$)OCH_2—$, $C_{1-6}$ alkoxy, amino di-substituted with $C_{1-6}$ alkyl groups, $NHC(O)R_3—$, $—C(O)NH—R_3$, $—OC(O)R_3$, and $—C(O)OR_3—$, wherein $R_3$ is $C_{1-6}$ alkyl d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from $C_{1-8}$ alkyl, linear or branched $C_{2-8}$ alkenyl, $C_{5-6}$ cycloalkyl, phenyl as defined in b), 5-6 membered aromatic ring group, halogen, $(C_{1-6}$alkyl$)OCH_2—$, $C_{1-6}$alkoxy, amino di-substituted with $C_{1-6}$ alkyl groups, $NHC(O)R_3—$, $—C(O)NH—R_3$, $—OC(O)R_3$, and $—C(O)OR_3—$, wherein $R_3$ is $C_{1-6}$ alkyl, and e) $—CH(R_4)—CH(R_5)COOH$, wherein $R_4$ is selected from H, $NH_2$, OH and $CH_2COOH$, and wherein $R_5$ is selected from H, $NH_2$, OH and $CH_2COOH$ for the preparation of a medicament for the prevention and/or treatment of a pathology associated with proinflammatory conditions, a disease associated with oxidative stress or production of reactive oxygen species or a skin pigmentation disorder.

"Alkyl" refers to a linear or branched hydrocarbon chain radical consisting of carbon and hydrogen atoms, containing no unsaturation, and which is attached to the rest of the molecule by a single bond. In a preferred embodiment, the alkyl groups have 1, 2, 3, 4, 5, 6, 7 or 8 carbon atoms. Methyl, ethyl, n-propyl, iso-propyl and butyl, pentyl, hexyl, heptyl, including n-butyl, tert-butyl, sec-butyl and iso-butyl are particularly preferred alkyl groups. As used herein, the term alkyl, unless otherwise stated, refers to both cyclic and noncyclic groups, although cyclic groups will comprise at least three carbon ring members, such as cyclopropyl or cyclohexyl. Alkyl radicals may be optionally substituted by one or more substituents, such as an aryl group, like in benzyl or phenethyl. In a more preferred embodiment, the alkyl is $C_1$-$C_6$ alkyl. In a more preferred embodiment, the $C_1$-$C_6$ alkyl is selected from the group consisting of $—CH_3$, $—CH_2CH_3$, $—(CH_2)_2CH_3$, $—(CH_2)_3CH_3$, $—(CH_2)_4CH_3$ and $—(CH_2)_5CH_3$.

"Alkenyl" refers to an unsaturated branched, straight-chain, or cyclic hydrocarbon group having at least one carbon-carbon double bond derived by the removal of one hydrogen atom from a single carbon atom of a parent alkene. In the context of the present invention, the alkenyl groups have 1, 2, 3, 4, 5, 6, 7 or 8 carbon atoms. The group may be in either the Z- or E- form (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. An alkenyl group having 2 to 8 carbon atoms is referred as a $—(C_2$-$C_8)$ alkenyl group.

The term "halo" or "halogen" means fluorine, chlorine, bromine or iodine.

The term "halo alkyl" refers to an alkyl group as defined above wherein at least one of the hydrogen atoms has been replaced by a halogen atom such as for example $CF_3$, $CHF_2$, $CH_2F$, $CF_2CF_3$ etc.

"Alkoxy" refers to a radical —OR where R represents an alkyl group as defined herein. In particular the term "$C_{1-6}$ alkoxy" refers to a radical —OR where R is an alkyl group having from 1 to 6 carbon atoms. Representative examples include, but are not limited to, methoxy, ethoxy, propoxy, butoxy, cyclohexyloxy, and the like.

"Cycloalkyl" refers to a saturated or unsaturated, but non-aromatic, cyclic alkyl group. In the context of the present invention the cycloalkyl group can be $C_{5-8}$ cycloalkyl, such as cyclopentane or cyclohexane.

The term "bicyclic ring" refers to two cyclic groups fused to form a bicyclic group, wherein one of the cyclic groups is a phenyl group and the other cyclic group is a $C_{5-8}$ aromatic heterocyclic group having one or more heteroatoms selected from N, S, and O. The phenyl group of the bicyclic ring may optionally substituted with $C_{1-8}$ alkyl, linear or branched $C_{2-8}$ alkenyl, $C_{5-8}$ cycloalkyl, phenyl optionally substituted with one or more groups independently selected from $C_{1-8}$ alkyl, $C_{2-8}$ alkenyl, halogen, phenyl, $C_{1-8}$ alkoxy, amine di-substituted with $C_{1-6}$ alkyl groups independently selected, $—NHC(O)R_3—$, $—C(O)NH—R_3$, $—OC(O)R_3$, and $—C(O)OR_3$, wherein $R_3$ is $C_{1-6}$ alkyl, 5-6 membered aromatic ring group, halogen, ($C_{1-6}$alkyl)$OCH_2$—, $C_{1-6}$ alkoxy, amino di-substituted with $C_{1-6}$ alkyl groups, $NHC(O)R_3$—, —$C(O)NH$—$R_3$, —$OC(O)R_3$, and —$C(O)OR_3$—, wherein $R_3$ is $C_{1-6}$ alkyl.

"Aryl" as used herein relates to single and multiple ring compounds, including multiple ring compounds that contain separate and/or fused aryl groups. Typical aryl groups contain from 1 to 3 separated and/or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl. The term includes but is not limited to, phenyl, naphthyl, tetrahydronaphthyl, indanyl, indenyl, and the like. In a preferred embodiment the aryl is phenyl.

"Heterocyclic", "heterocyclo" or "heterocyclyl" refer to cyclic hydrocarbon group in which one or more carbon atoms (and any associated hydrogen atoms) are independently replaced with the same or a different heteroatom selected from N, O, and S. In some embodiments, a heterocyclyl group includes 3 to 10 ring members of which 1, 2, or 3 ring members are independently selected from N, O, or S. In other embodiments, a heterocyclyl group includes 5 to 7 ring members of which 1, 2, or 3 are heteroatoms independently selected from N, O, or S.

The term "optionally substituted" means unsubstituted or substituted with one or more substituents having one or more different functional groups in one or more positions. As understood in this technical area, there can be a certain degree of substitution on the previously defined radicals. The term "substituted" whether preceded by the term "optionally" or not, and substituents contained in formulas of the invention, refer to the replacement of hydrogen radicals in a given structure with the radical of a specified substituent. When more than one position in any given structure may be substituted with more than one substituent selected from a specified group, the substituent may be the same or different at every position.

In one embodiment, the compound for use according to the invention is the compound of formula:

(II)

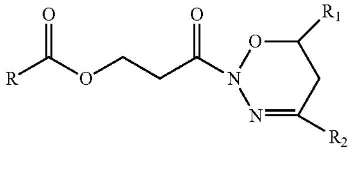

or (III)

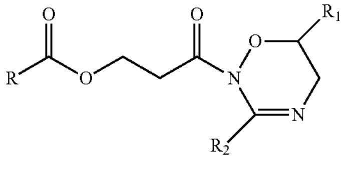

or a pharmaceutically acceptable salt, stereoisomer or solvate thereof.

In a particular embodiment, the invention refers to the compound for use according to the invention wherein $R_1$ and $R_2$ are the same group, or to a pharmaceutically acceptable salt, stereoisomer or solvate thereof. Preferably, $R_1$ and $R_2$ are —$(CH_2)_4$—$CH_3$. Therefore, the compound for use according to the invention is selected from:

(IV)

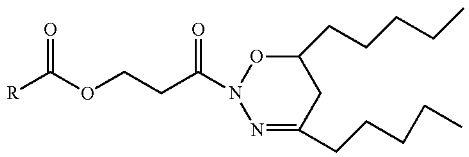

and (V)

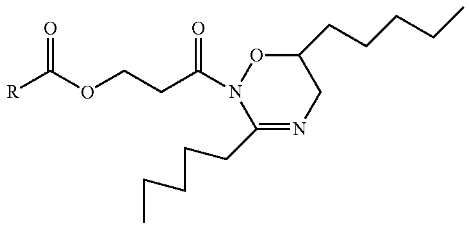

or a pharmaceutically acceptable salt, stereoisomer or solvate thereof. In a more preferred embodiment the compound for use according to the invention is compound (IV). In another preferred embodiment, the compound for use according to the invention is compound (V).

In one particular embodiment the invention refers to the compound for use according to the invention wherein R is a methyl group or —$(CH_2)_2$—COOH, or a pharmaceutically acceptable salt, stereoisomer or solvate thereof. Therefore, the compound for use according to the invention is selected from:

(IIa)

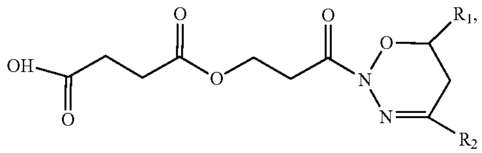

(IIIa)

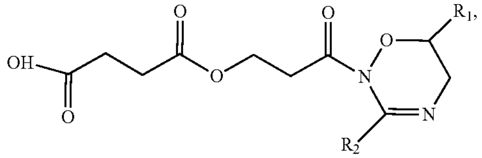

(IIb)

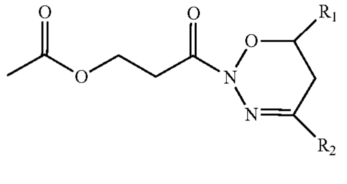

and (IIIb)

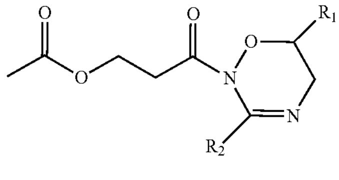

In a more preferred embodiment R is a methyl group, and $R_1$ and $R_2$ are $—(CH_2)_4—CH_3$. Therefore, the compound for use according to the invention is selected from:

(VI)

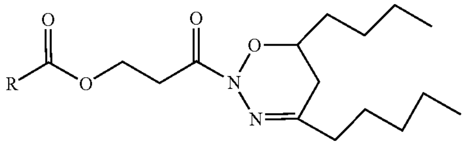

and (VII)

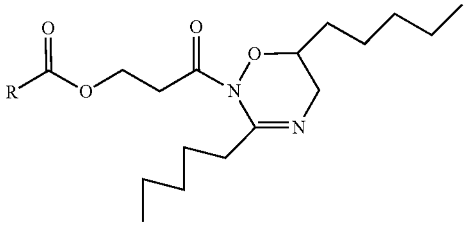

In another preferred embodiment R is $—(CH_2)_2—COOH$ and $R_1$ and $R_2$ are $—(CH_2)_4—CH_3$. Therefore the compound for use according to the invention is:

(VIII)

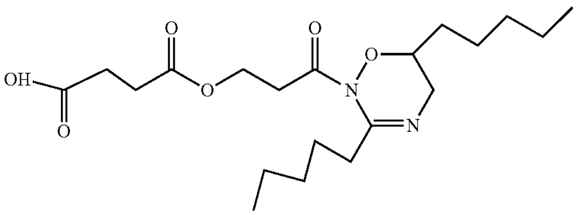

In another preferred embodiment, the compound for use in the invention is (IX)

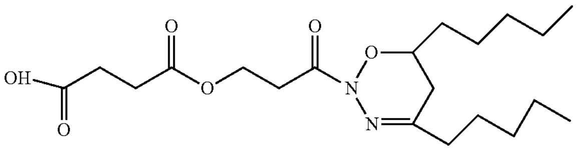

Compounds IX and VI are referred in the context of the present invention as DOXA-1 and DOXA-2 respectively.

In a more preferred embodiment the compound for use according to the invention is

DOXA-1

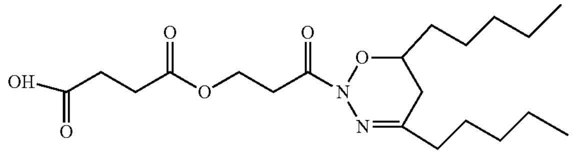

In another preferred embodiment, the compound for use according to the invention is

DOXA-2

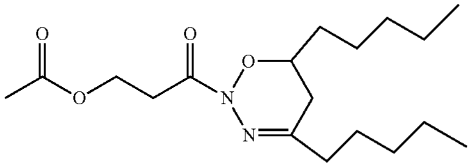

The invention also relates to a pharmaceutically acceptable salt, stereoisomer or solvate of a compound for use according to the invention for use according to the invention.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition includes in particular physiologically acceptable salts; this term must be understood as equivalent to "pharmacologically acceptable salts" or "pharmaceutically acceptable salts".

The term "physiologically acceptable salt" or "pharmaceutically acceptable salt" is understood in particular, in the context of this invention, as a salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of both. Generally, non-aqueous media like ether, ethyl acetate, ethanol, 2-propanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts. Since hydroxytyrosol has three hydroxyl groups, alkali addition salts are particularly preferred such as $Na^+$ and $NX_4^+$ (wherein X is independently selected from H or a $C_1$-$C_4$ alkyl group).

For those persons skilled in the art, it will be evident that the scope of the present invention also includes salts which are not pharmaceutically acceptable as possible means for obtaining pharmaceutically acceptable salts for the uses of the invention.

Any compound referred to herein is intended to represent such specific compound as well as certain variations or forms. The compounds for use according to the present invention represented by the above described formula (I) include stereoisomers. The term "stereoisomer" as used herein includes any enantiomer, diastereomer or geometric isomer (E/Z) of such compound. In particular, compounds referred to herein may have asymmetric centres and therefore exist in different enantiomeric or diastereomeric forms. Thus, any given compound referred to herein is intended to represent any one of a racemate, one or more enantiomeric forms, one or more diastereomeric forms, and mixtures thereof.

Likewise, stereoisomerism or geometric isomerism related to a double bond is also possible, therefore in some cases the molecule could exist as (E)-isomer or (Z)-isomer (trans and cis isomers). If the molecule contains several double bonds, each double bond will have its own stereoisomerism, that could be the same or different than the stereoisomerism of the other double bonds of the molecule. All the stereoisomers including enantiomers, diastereoisomers and geometric isomers of the compounds referred to herein, and mixtures thereof, are considered within the scope of the present invention.

The compounds for use according to the invention may be in crystalline form either as free compounds or as solvates (e.g. hydrates, alcoholates, particularly methanolates) and it is intended that both forms are within the scope of the present invention. Solvate may include water or non-aqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include stoichiometric hydrates as well as compositions containing variable amounts of water. Methods of solvation are generally known within the art.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e. the capacity to occur in different crystalline forms). These different crystalline forms are typically known as "polymorphs". It is to be understood that when named or depicted by structure, the disclosed compounds and solvates (e.g., hydrates) also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

Furthermore, any compound referred to herein may exist as tautomers. Specifically, the term tautomer refers to one of two or more structural isomers of a compound that exist in equilibrium and are readily converted from one isomeric form to another. Common tautomeric pairs are enamine-imine, amide-imidic acid, keto-enol, lactam-lactim, etc.

Unless otherwise stated, the compounds for use according to the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by 13C- or 14C-enriched carbon, or the replacement of at least one nitrogen by 15N-enriched nitrogen are within the scope of this invention.

The compounds of formula (I) or their salts or solvates for use according to the invention are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its pharmaceutically acceptable salt, stereoisomer or solvate.

The invention also relates to uses according to the invention of metabolites of the compounds described in the present description. A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups.

The invention also relates to prodrugs of the compounds for use according to the invention. The term "prodrug", as used herein, is intended to represent covalently bonded carriers, which are capable of releasing the compound of formula (I) as active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like.

In additional preferred embodiments, the preferences described above for the different groups and substituents in the formulae above are combined. The present invention is also directed to the uses of such combinations.

The compounds for use in the present invention, may be a pharmaceutical composition comprising the compound for use according to the invention or a pharmaceutically acceptable salt, stereoisomer or solvate thereof and a pharmaceutically acceptable excipient.

"Pharmaceutical composition" as used herein, relates to compositions and molecular entities that are physiologically tolerable and do not typically produce an allergic reaction or a similar unfavorable reaction as gastric disorders, dizziness and suchlike, when administered to a human or animal. Preferably, the term "pharmaceutically acceptable" means it is approved by a regulatory agency of a state or federal government or is included in the U.S. Pharmacopoeia or other generally recognized pharmacopoeia for use in animals, and more particularly in humans.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005; or "Handbook of Pharmaceutical Excipients", Rowe C. R.; Paul J. S.; Marian E. Q., sixth Edition.

Appropriate amounts of a compound of formula (I) as defined above, or a pharmaceutically acceptable salt, stereoisomer or solvate thereof can be formulated with pharmaceutically acceptable excipients and/or carriers to obtain a pharmaceutical composition for use in the medical uses of the invention.

Suitable pharmaceutically acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and similars.

The pharmaceutical compositions containing the compound of formula (I) as defined above, or a pharmaceutically acceptable salt, stereoisomer or solvate thereof for use according to the invention can occur at any pharmaceutical form of administration considered appropriate for the selected administration route, for example, by systemic (e.g intravenous, subcutaneous, intramuscular injection), oral, parenteral or topical administration, for which it will include the pharmaceutically acceptable excipients necessary for formulation of the desired method of administration. Additionally, it is also possible to administer the composition comprising the compound of formula (I) as defined above, or a pharmaceutically acceptable salt, stereoisomer or solvate thereof for use according to the invention intranasally or sublingually which allows systemic administration by a non-aggressive mode of administration. Also, intraventricular administration may be adequate. A preferred route of delivery is oral.

Those skilled in the art are familiar with the principles and procedures discussed in widely known.

Where necessary, the compound of formula (I) as defined above, or a pharmaceutically acceptable salt, stereoisomer or solvate thereof for use according to the invention is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a compound of the present invention including encapsulation in liposomes, microparticles, microcapsules and the like.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration, compounds of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, the compounds of formula (I) as defined above, or a pharmaceutically acceptable salt, stereoisomer or solvate thereof for use according to the invention may be administered in the form of transdermal patches or iontophoresis devices. In one embodiment, the compounds for use according to the invention are administered as a transdermal patch, for example, in the form of sustained-release transdermal patch. Suitable transdermal patches are known in the art.

Several drug delivery systems are known and can be used to administer the agents or compositions for use according to the invention, including, for example, encapsulation in liposomes, microbubbles, emulsions, microparticles, microcapsules and similars. The required dosage can be administered as a single unit or in a sustained release form.

Sustainable-release forms and appropriate materials and methods for their preparation are described in, for example, “Modified-Release Drug Delivery Technology”, Rathbone, M. J. Hadgraft, J. and Roberts, M. S. (eds.), Marcel Dekker, Inc., New York (2002), “Handbook of Pharmaceutical Controlled Release Technology”, Wise, D. L. (ed.), Marcel Dekker, Inc. New York, (2000). In one embodiment of the invention, the orally administrable form of a compound for use according to the invention is in a sustained release form further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of the them. Enteric coatings may be applied using conventional processes known to experts in the art, as described in, for example, Johnson, J. L., “Pharmaceutical tablet coating”, Coatings Technology Handbook (Second Edition), Satas, D. and Tracton, A. A. (eds), Marcel Dekker, Inc. New York, (2001), Carstensen, T., “Coating Tablets in Advanced Pharmaceutical Solids”, Swarbrick, J. (ed.), Marcel Dekker, Inc. New York (2001), 455-468.

The term “prevention”, “preventing” or “prevent”, as used herein, relates to the administration of a compound according to the invention or of a medicament comprising said compound to a subject who has not been diagnosed as possibly having a disease, but who would normally be expected to develop said disease or be at increased risk for said disease. The prevention intends to avoid the appearance of said disease. The prevention may be complete (e.g. the total absence of a disease). The prevention may also be partial, such that for example the occurrence of a disease in a subject is less than that which would have occurred without the administration of the compound of the present invention. Prevention also refers to reduced susceptibility to a clinical condition.

The term “treatment”, as used herein, refers to any type of therapy, which is aimed at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, “treatment,” “treating,” and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, “treatment” includes (1) preventing the disorder from occurring or recurring in a subject, (2) inhibiting the disorder, such as arresting its development, (3) stopping or terminating the disorder or, at least, symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter.

The term “subject” as used herein, relates to any subject, particularly a mammalian subject, for whom therapy is desired. Mammalian subjects include humans, domestic animals, farm animals, and zoo, sports, or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human.

The inventors have observed that the compounds of formula (I) show anti-inflammatory activity. In addition, the compounds of formula (I) can inhibit TNF-α activity and NF-ηB which are known to be involved in several inflammatory diseases. Therefore, in a preferred embodiment, the invention relates to the compounds of formula (I) for use in the prevention and or treatment of a pathology associated with proinflammatory conditions.

“Pathology associated with proinflammatory conditions”, as used herein relates to disease caused by inflammation. Pro-inflammatory conditions are usually related with excess level of pro-inflammatory markers in blood such as IL-1α, β, IL-2, IL-3, IL-6, IL-7, IL-9, IL-12, IL-17, IL-18, TNF-α, LT, LIF, Oncostatin, and IFNc1α, β, γ. The term proinflammatory condition includes both acute and chronic inflammatory disorders. The term “acute inflammatory disorder” is intended to include disorders, and episodes of disorders, characterized by rapid onset of symptoms associated with an inflammatory response and relatively short duration of symptoms, whereas a “chronic inflammatory disorder” is intended to include disorders characterized by the continued presence of symptoms associated with an inflammatory response and ongoing duration of symptoms.

Examples of diseases related to a proinflammatory condition are acute and chronic seropositive or seronegative, neurodegenerative diseases, age-related macular degeneration, systemic autoimmune diseases such as systemic lupus erythematosus, TNF-α dependent cellular degeneration, cachexia and autocrine and paracrine pathological cell growth, organ specific autoimmune diseases such as myasthenia gravis, multiple sclerosis, demyelinating diseases, meningitis, encephalitis, meningoencephalitis, inflammatory radiculopathies, peripheral neuropathies, inflammatory vacultides (e.g. polyarteritis nodosa, Wegner’s granulomatosis, Takayasu’s arteritis, temporal arteritis, and lymphomatoid granulomatosus), vasculitis, artery occlusion, heart failure, ischemic disease, myocarditis, pericarditis, chronic obstructive pulmonary disease, interstitial lung disease, pulmonary fibrosis (e.g., idiopathic pulmonary fibrosis), metabolic syndrome, asthma, allergic rhinitis, periodontal disease, chronic hepatitis, hepatitis, cirrhosis, celiac disease, diabetes, inflammatory Bowel Disease, tubulointerstitial nephritis, glomerulonephritis, renal failure, inflammatory cystitis, prostatitis, benign prostatic hyperplasia, rheumatoid arthritis, osteoarthritis, olygoarthritis, polyarthritis, spondiloarthropathies, inflammatory osteolysis, undifferentiated spondyloarthropathy, undifferentiated arthropathy, amyloidosis or sarcoidosis, dermatomyositis, atherosclerosis, colagenopathies, atopic dermatitis, sepsis, thyroiditis or insulinitis, organ transplantation, multiorganic failure, graft versus host disease, post-traumatic vascular angioplasty (e.g. restenosis after angioplasty), inflammatory osteolysis, allergic disorders, septic shock, apoptosis, necrosis.

In a preferred embodiment, the proinflammatory condition is selected from the group consisting of skin diseases, such as psoriasis, eczema, vitiligo, impetigo, acne, melanoma, rosacea, urticaria, melasma and alopecia.

In another preferred embodiment, the proinflammatory condition is selected from the group consisting of rheumatoid arthritis, artery occlusion, diabetes, neurodegenerative diseases, osteoarthritis, atherosclerosis, asthma, psoriasis, periodontal disease and age related macular degeneration.

Tyrosinase is an enzyme that catalyzes the process of neuromelanin production in which the oxidation of dopamine produces dopaquinones. However, excessive production of dopaquinones results in neuronal damage and cell death. This suggests that tyrosinase might play a significant role in neuromelanin formation in the human brain and responsible for the neurodegeneration associated with Parkinson's disease and Huntington's diseases.

The inventors have observed that the compounds of formula (I) are tyrosinase inhibitors. Therefore, in a preferred embodiment the neurodegenerative diseases treated by the medical use of the invention is Parkinson's disease or Huntington's disease.

Hypoxia inducible factor-1 (HIF-1) is a transcriptional factor responsible for cellular and tissue adaption to low oxygen tension. HIF-1, a heterodimer consisting of a constitutively expressed β subunit and an oxygen-regulated a subunit, regulates a series of genes that participate in angiogenesis, iron metabolism, glucose metabolism, and cell proliferation/survival. It is known that HIF-1 is a medicinal target for the neurodegenerative diseases. The inventors have observed that the compounds of formula (I) are HIF-1 inhibitors. Therefore, in a preferred embodiment the compounds of formula (I) are for use in the prevention and/or treatment of a neurodegenerative disease, particularly Alzheimer's disease, Parkinson's disease, Huntington's disease or amyotrophic lateral sclerosis.

Moreover, STAT3 has recently emerged as a key player in the development and pathogenesis of psoriasis and psoriatic-like inflammatory conditions. The inventors have observed that the compounds of formula (I) are capable of inhibiting STAT3. Therefore, in another preferred embodiment the compounds of formula (I) are for use in the treatment of psoriasis or psoriatic-like inflammatory conditions.

The inventors have also shown that the compounds of formula (I) have antioxidant activity. Therefore, in another aspect, the compounds of formula (I), as described above, are for use in the prevention and/or treatment of a disease associated with oxidative stress or production of reactive oxygen species.

"Disease associated with oxidative stress or production of reactive oxygen species", as used herein, relates to a condition of a subject characterized by an oxidative stress wherein in said subject any harmful effect or symptom of oxidative stress can be shown, assessed, measured or diagnosed.

"Oxidative stress", as used herein relates to the state of a subject characterized by an imbalance between reactive oxygen species (ROS) and antioxidant defence capacity or the subject, i.e. an increased level of ROS, in particular superoxide anion radical ($O_2^-$), hydrogen peroxide ($H_2O_2$) and hydroxyl free radical (—OH). Production of reactive oxygen species is a particularly destructive aspect of oxidative stress. Such species include free radicals, aldehydes and peroxides. Some of the less reactive of these species (such as superoxide) can be converted by oxidoreduction reactions with transition metals or other redox cycling compounds (including quinones) into more aggressive radical species that can cause extensive cellular damage. Damage of macromolecules due to oxidative stress is related to loss of optimal function of various organs and aging. Oxidative stress is also directly related to premature aging.

In a preferred embodiment the disease associate with oxidative stress or production of reactive oxygen species is selected from the group consisting of ischemia-reperfusion injury, a liver disease, age-related immune deficiency and premature aging disorders, age-related macular degeneration, retinal detachment, hypertensive retinal disease, uveitis, degenerative retinal damage, cataractogenesis, retinopathy, Meuniere's disease, drug-induced toxicity, idiopathic otitis, gastrointestinal diseases, musculoskeletal diseases, cardiovascular diseases, neurodegenerative diseases and cerebrovascular diseases. In a more preferred embodiment, the disease associate with oxidative stress or production of reactive oxygen species is a neurodegenerative disease, more preferably Alzheimer's, Parkinson's, Huntington's or tardive dyskinesia.

In another preferred embodiment the disease associate with oxidative stress or production of reactive oxygen species is selected from the group consisting of cerebrovascular diseases, cardiovascular diseases, respiratory diseases, musculoskeletal diseases, gastrointestinal diseases, age-related immune deficiency and premature aging disorders, ear diseases, eye diseases, drug-induced toxicity. In a more preferred embodiment, the disease associate with oxidative stress or production of reactive oxygen species is a neurodegenerative disease, more preferably Alzheimer's, Parkinson's, Huntington's or tardive dyskinesia.

The inventors have also shown that the compounds of formula (I) are tyrosinase inhibitors. Tyrosinase is an oxidase that is the rate-limiting enzyme for controlling the production of melanin. Decreasing tyrosinase activity has been targeted for the treatment of conditions related to the hyperpigmentation of the skin. Therefore, in a preferred embodiment, the compound of formula (I) according to the invention is for use in the prevention and/or treatment of a skin pigmentation disorder.

The term "skin pigmentation disorder", as used herein, relates to a disorder in the production of melanin, preferably a disorder due to hyperpigmentation, more preferably the disorder is melasma, drug-induced hyperpigmentation, acanthosis nigricans, lentigines, Addison's disease or hemochromatosis.

For use in the prevention and/or treatment according to the invention, the compound of formula (I) or a pharmaceutically acceptable salt, solvate or isomer thereof or the pharmaceutical composition of the invention is present in an effective amount.

The term "effective" amount or a "therapeutically effective amount" of a drug or pharmacologically active agent is meant a nontoxic but sufficient amount of the drug or agent to provide the desired effect.

Even though individual needs vary, determination of optimal ranges for effective amounts of the agent of the invention belongs to the common experience of those experts in the art. In general, the dosage needed to provide an effective amount of such compound, which can be adjusted by one expert in the art will vary depending on age, health, fitness, sex, diet, weight, frequency of treatment and the nature and extent of impairment or illness, medical condition of the patient, route of administration, pharmacological considerations such as activity, efficacy, pharmacokinetic and toxicology profile of the particular compound used, if using a system drug delivery, and if the compound is administered as part of a combination of drugs.

The effective quantity of the compound for use according to the invention can vary within a wide range and, in general, will vary depending on the particular circumstances of application, duration of the exposure and other considerations. In a particular embodiment, the dose ranges between 0.05 mg/kg and 50 mg/kg, more preferably between 1 mg/kg and 20 mg/kg.

In a preferred embodiment the effective amount is between about between about 0.005% and about 0.04% weight, between about 0.0075% weight and about 0.0375% weight, between about 0.001% weight and about 0.035% weight, between about 0.00125% weight and about 0.0325% weight, between about 0.0015% weight and about 0.0325% weight, between about 0.00175% weight and about 0.03% weight, and more preferably between about 0.0018% weight and about 0.032% weight. In a particular embodiment, the effective amount is between about 0.005% and about 0.02% weight, preferably between about 0.005% weight and about 0.015% weight, more preferably between about 0.005% weight and about 0.01% weight. In some embodiments the effective amount is about 0.001% weight, about 0.002% weight, about 0.003% weight or about 0.004% weight. The percentages (% w/w) are expressed as weight of the compound of formula (I) or a pharmaceutically acceptable salt, solvate or isomer thereof by the total weight of the composition comprising the compound or by weight of the foodstuff, foodstuff package, medical device or surface.

In another embodiment the effective amount is expressed in μg/mL or μg/g (μg of the compound of formula (I) or a pharmaceutically acceptable salt, solvate or isomer thereof by mL or g of the composition comprising the compound), therefore effective amount is about 75 and about 375 μg/mL (or μg/g), between about 100 and about 350 μg/mL (or μg/g), between about 125 and about 325 μg/mL (or μg/g), between about 150 and about 325 μg/mL (or μg/g), between about 175 and about 300 μg/mL (or μg/g), and more preferably between about 180 and about 320 μg/mL (or μg/g). In a particular embodiment, the effective amount is between about 50 and about 200 μg/mL (or μg/g), preferably between 50 and about 150 μg/mL (or μg/g), more preferably between about 50 and about 100 μg/mL (or μg/g). In some embodiments the effective amount is about 100 μg/mL (or μg/g), about 200 μg/mL (or μg/g), about 300 μg/mL (or μg/g) or about 400 μg/mL (or μg/g).

When the compound of formula (I) or a salt, solvate or isomer thereof as defined herein for use according to the invention is present on a surface, it is preferably in an effective amount of between about 1 and about 200 μg/$cm^2$, preferably between about 1 and about 100 μg/$cm^2$, preferably between about 1 and about 50 μg/$cm^2$, more preferably between about 5 and about 300 μg/$cm^2$.

In additional preferred embodiments, the preferences described above for the different groups and substituents in the formulae above are combined. The present invention is also directed to such combinations. The present invention covers any combination of compounds and diseases.

Cosmetic Method

Tyrosinase is a key enzyme which catalyzes a rate-limiting step of the melanin synthesis. An excessive production of melanin causes dermatological problems such as freckles, solar lentigo (age spots) and melasma. Upregulation of TNF-α is a key early response to UVB by keratinocytes and represents an important component of the inflammatory cascade in skin. In addition, it is known that NF-ηB is activated upon UV irradiation and induces IL-1, TNF-α and matrix metalloprotease-1. The inventors have demonstrated that the compounds of formula (I) are tyrosinase inhibitors, as well as TNF-α and NF-ηB inhibitors and act as antioxidants compounds. Therefore, the compounds of formula (I) are suitable in cosmetic methods for preventing and/or treating skin aging, irradiated skin or for skin whitening.

Therefore, in another aspect, the invention relates to a cosmetic method for preventing and/or treating skin aging, irradiated skin or for skin-whitening comprising administering a compound of formula (I) or a cosmetically acceptable salt, stereoisomer or solvate thereof (I)

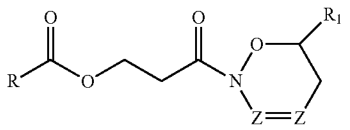

wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)$OCH_2$—, amine di-substituted with $C_{1-6}$ alkyl groups independently selected, b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)$R_3$—, —C(O)NH—$R_3$, —OC(O)$R_3$, and —C(O)$OR_3$—, wherein $R_3$ is $C_{1-6}$ alkyl, c) 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl, phenyl as defined in b), 5-6 membered aromatic ring group, halogen, ($C_{1-6}$alkyl)$OCH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)$OR_3$—, wherein $R_3$ is $C_{1-6}$ alkyl d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from $C_{1-8}$ alkyl, linear or branched $C_{2-8}$ alkenyl, $C_{5-6}$ cycloalkyl, phenyl as defined in b), 5-6 membered aromatic ring group, halogen, ($C_{1-6}$alkyl)$OCH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)$OR_3$—, wherein $R_3$ is $C_{1-6}$ alkyl, and e) —CH($R_4$)—CH($R_5$)COOH, wherein $R_4$ is selected from H, $NH_2$, OH and $CH_2COOH$, and wherein $R_5$ is selected from H, $NH_2$, OH and $CH_2COOH$ to a subject in need thereof.

In one embodiment, the compound for use in the method according to the invention is the compound of formula:

(II)

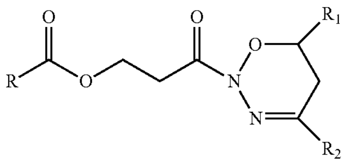

or (III)

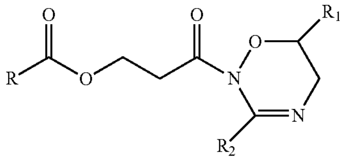

or a cosmetically acceptable salt, stereoisomer or solvate thereof.

In a particular embodiment, the invention refers to the compound for use in the method of the invention wherein $R_1$ and $R_2$ are the same group, or to a pharmaceutically acceptable salt, stereoisomer or solvate thereof. Preferably, $R_1$ and $R_2$ are $-(CH_2)_4-CH_3$. Therefore, the compound for use in the method according to the invention is selected from:

(IV)

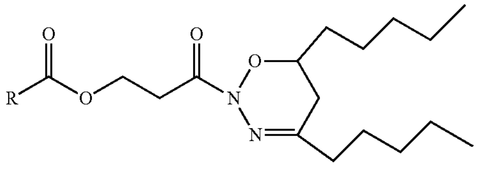

and (V)

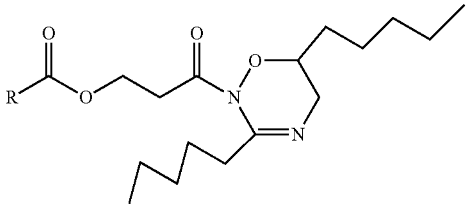

or a cosmetically acceptable salt, stereoisomer or solvate thereof. In a more preferred embodiment the compound for use in the method according to the invention is compound (IV).

In one particular embodiment the invention refers to the compound for use in the method according to the invention wherein R is a methyl group or $-(CH_2)_2-COOH$, or a pharmaceutically acceptable salt, stereoisomer or solvate thereof. Therefore, the compound for the method of the invention is selected from:

(IIa)

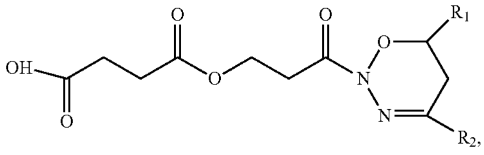

-continued (IIIa)

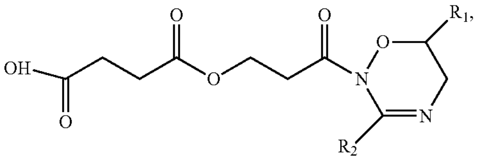

(IIb)

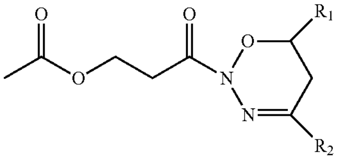

and (IIIb)

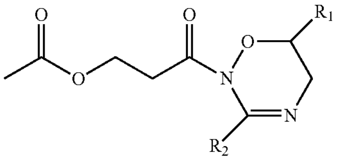

In a more preferred embodiment R is a methyl group, and $R_1$ and $R_2$ are $-(CH_2)_4-CH_3$. Therefore, the compound in the method of the invention is selected from:

(VI)

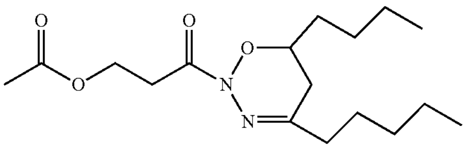

and (VII)

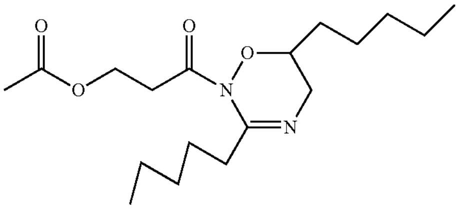

In another preferred embodiment R is $-(CH_2)_2-COOH$ and $R_1$ and $R_2$ are $-(CH_2)_4-CH_3$. Therefore the compound in the method of the invention is:

(VIII)

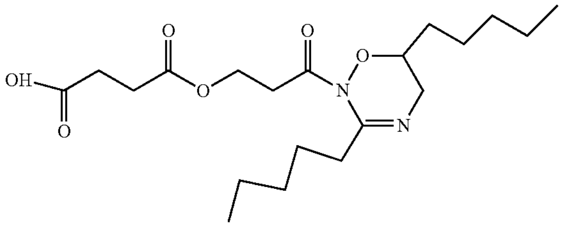

In another preferred embodiment, the compound in the method of the invention is (IX)

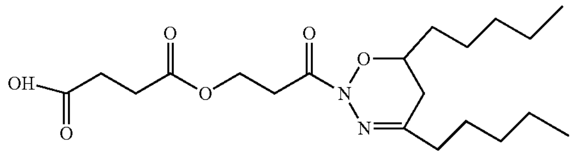

Compounds IX and VI are referred in the context of the present invention as DOXA-1 and DOXA-2 respectively.

In a more preferred embodiment the compound is

DOXA-1

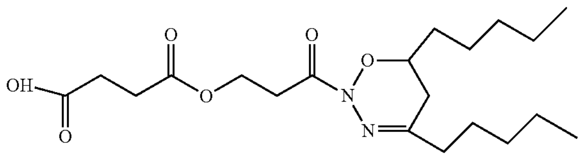

In another preferred embodiment, the compound is

DOXA-2

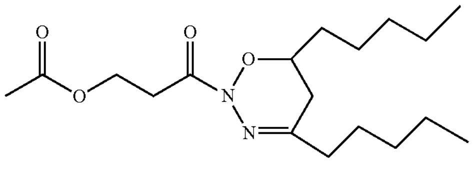

As used herein, the term "cosmetic method" relates to a method used to enhance the appearance of the skin in a subject. Cosmetic compositions used in the cosmetic method of the invention include skin-care creams, lotions, powders, lipsticks, eye and facial makeup, towelettes, gels, deodorants, hand sanitizer, baby products, bath oils, bubble baths, bath salts, butters and many other types of products.

"Skin aging", as used herein relates to a multi-factorial process of the skin that affects nearly every aspect of its biology and function; it is driven by both intrinsic (e.g., time, genetic factors, hormones) and extrinsic (e.g., UV exposure, pollution, cigarette smoke) factors. Skin aging is also produced by senescence. The cosmetic adverse effects of aging relates to characteristics of intrinsic or chronological aging and include as a way of illustrative non limitative examples, visible signs such as thin and dry skin, fine wrinkles, decreased elasticity, aberrant pigmentation, hair graying and hair loss.

In a preferred embodiment the skin aging is photoaging. The term "photoaging" relates to the processes due to the prolonged exposure of the skin to ultraviolet radiation or HEV (also known as high energy visible light, or blue light) which result in the premature aging of the skin, and it presents the same physical characteristics as aging, such as and not restricted to, flaccidity, sagging, changes to the color or irregularities in the pigmentation, abnormal and/or excessive keratinization.

"Irradiated skin", as used herein relates to the damage on the skin caused by general radiation that can damage cells by directly disrupting DNA or through free radical production. The skin reactions include dryness, epilation, pigmentation changes and erythema.

"Skin whitening", also known as lightening, brightening, depigmentation, and bleaching is the treatment to lighten skin color, usually by reducing the skin's melanin content.

The compounds for use according to the cosmetic method of the invention may be in the form of a cosmeceutical, nutraceutical or cosmetic composition.

As used herein, the term "cosmeceutical product" refers to a product suitable for use in the body or animal body comprising one or more cosmeceutical products (functional cosmetics, dermaceuticals or active cosmetics), i.e., topical hybrid products with cosmetic-pharmaceutical characteristics containing active ingredients having effect on user's skin, hair and/or nails, at higher and more effective concentrations, therefore they are located in an intermediate level between cosmetic and drug. Illustrative examples of cosmeceutical products include essential oils, ceramides, enzymes, minerals, peptides, vitamins, etc.

As used herein, the term "nutraceutical product" refers to a product suitable for use in human beings or animals, comprising one or more natural products with therapeutic action which provide a health benefit or have been associated with disease prevention or reduction, and it includes dietary supplements presented in a non-food matrix (e.g., capsules, powder, etc.) of a concentrated natural bioactive product usually present (or not) in the foods and which, when taken in a dose higher than that existing in those foods, exerts a favorable effect on health which is greater than effect which the normal food may have. Therefore, the term "nutraceutical product" includes isolated or purified food products as well as additives or food supplements which are generally presented in dosage forms normally used orally, for example, capsules, tablets, sachets, drinkable phials, etc.; such products provide a physiological benefit or protection against diseases, generally against chronic diseases. If desired, the nutraceutical product provided by the invention can contain, in addition to the compound of formula (I), one or more nutraceuticals (products or substances associated with disease prevention or reduction), for example, flavonoids, omega-3 fatty acids, etc., and/or one or more prebiotics (non-digestible food ingredients which stimulate probiotic activity and/or growth), for example, oligofructose, pectin, inulin, galacto-oligosaccharides, lactulose, human milk oligosaccharides, dietary fiber, etc.

The term "cosmetic composition" or "personal care composition", as used herein, refers to a composition suitable for use in personal hygiene of human beings or animals, or in order to enhance the natural beauty or change the body appearance without affecting the structure or functions of the human or animal body, comprising one or more products providing such effects. If desired, the cosmetic composition provided by the invention can contain, in addition to the compound of formula (I) of the invention, one or more cosmetics or cosmetic products, i.e., substances or mixtures intended to be placed in contact with the external parts of the human or animal body (e.g., epidermis, hair system, nails, lips, etc.) or with the teeth and the buccal mucosa, for the exclusive or main purpose of cleaning them, perfuming them, changing their appearance, protecting them, keeping them in good condition or correcting body odors. Illustrative examples of cosmetically acceptable vehicles include the products contained in the INCI (International Nomenclature of Cosmetic Ingredients) list. Cosmetic or personal care compositions include products such as balms, pads, pomades, creams, etc. oils, surfactants, humectants, botanical extracts, vitamins, antioxidants, sunscreen agents, perfumes, preservatives, and the like.

The ingredients as described hereinabove are preferably provided in a cosmetic composition that may be formulated into a cream, gel, lotion, oil, ointment, powder, stick, cake, or other forms that can be topically applied. The resulting cosmetic composition may be in the form of a liquid, solid, semi-solid, dispersion, suspension, solution or emulsion, and it can be either aqueous-based or anhydrous. The cosmetic compositions of the invention may also be in the form of color cosmetic compositions, such as foundation makeup, mascara, lip color, blush, eye shadow, and the like.

In a particular and preferred embodiment of the invention, the compound of formula (I) is administered by topical route. Adequate formulations for topical administration of the composition of the invention are detailed in the context of the medical uses of the invention and equally apply to the cosmetic method of the invention.

If desired, the compound of formula (I) for the cosmetic method of the invention is incorporated in a fabric, a non-woven fabric or a medical device. Illustrative examples of said fabric, non-woven fabric or medical device include but are not limited to bandages, gauzes, t-shirts, panty hose, socks, underwear, girdles, gloves, diapers, sanitary napkins, dressings, bedspreads, towelettes, adhesive patches, non-adhesive patches, occlusive patches, microelectric patches and face masks.

The compound for use according to the method of the invention may be administered in a cosmetic effective amount.

The term "cosmetic effective amount", as used herein, relates to the sufficient amount of a compound of the invention to provide the desired effect and it will generally be determined, by among other causes, the characteristics of the compound itself and the cosmetic effect to be achieved. The dosage for obtaining a cosmetic effective amount it will also depend on a range of factors, such as, for example, age, weight, sex or tolerance of the animal, preferably a mammal and more preferably human.

In a particular and preferred embodiment of the cosmetic method of the invention, the cosmetic composition of the invention is administered by topical route. Adequate formulations for topical administration of the compound for use according to the invention have been detailed in the context of the medical uses of the invention and equally apply to the cosmetic method of the invention.

All the terms and embodiments previously described are equally applicable to this aspect of the invention.

Method for Inhibiting Enzymatic Browning

Browning in fruits and vegetables is of great concern to growers and the food industry as it impairs the organoleptic properties of the product. The rate of enzymatic browning depends on the concentration of active tyrosinase and phenolic compounds, oxygen availability, pH and temperature conditions in the tissue. The inventors have demonstrated that the compounds of formula (I) are tyrosinase inhibitors. Therefore, the compounds of the invention can be used in a method for inhibiting enzymatic browning.

Therefore, in one aspect, the invention relates to a method of inhibition of enzymatic browning in food or beverage which comprises contacting said food or beverage with a compound of formula (I) or a salt, stereoisomer or solvate thereof

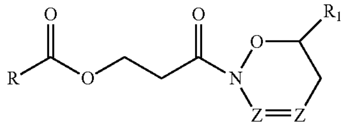
(I)

wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)$OCH_2$—, amine di-substituted with $C_{1-6}$ alkyl groups independently selected, b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)$R_3$—, —C(O)NH—$R_3$, —OC(O)$R_3$, and —C(O)O$R_3$—, wherein $R_3$ is $C_{1-6}$ alkyl, c) 5-6 membered aromatic ring having one or more heteroatoms selected from N, S, and O and being optionally substituted with one or more groups independently selected from:
   $C_{1-8}$ alkyl, linear or branched $C_{2-8}$ alkenyl, $C_{5-6}$ cycloalkyl,
   phenyl as defined in b),
   5-6 membered aromatic ring group,
   halogen,
   ($C_{1-6}$ alkyl)$OCH_2$—, $C_{1-6}$ alkoxy,
   amino di-substituted with $C_{1-6}$ alkyl groups,
   NHC(O)$R_3$—, —C(O)NH—$R_3$, —OC(O)$R_3$, and —C(O)O$R_3$—, wherein $R_3$ is $C_{1-6}$ alkyl d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from
   $C_{1-8}$ alkyl, linear or branched $C_{2-8}$ alkenyl, $C_{5-6}$ cycloalkyl,
   phenyl as defined in b),
   5-6 membered aromatic ring group,
   halogen,
   ($C_{1-6}$ alkyl)$OCH_2$—, $C_{1-6}$ alkoxy,
   amino di-substituted with $C_{1-6}$ alkyl groups,
   NHC(O)$R_3$—, —C(O)NH—$R_3$, —OC(O)$R_3$, and —C(O)O$R_3$—, wherein $R_3$ is $C_{1-6}$ alkyl, and e) —CH($R_4$)—CH($R_5$)COOH, wherein $R_4$ is selected from H, $NH_2$, OH and $CH_2COOH$, and wherein $R_5$ is selected from H, $NH_2$, OH and $CH_2COOH$ under conditions sufficient to inhibit enzymatic browning of said food or beverage.

In one embodiment, the compound according to the invention is the compound of formula:

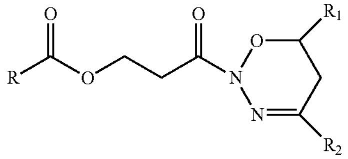
(II)

or

-continued (III)

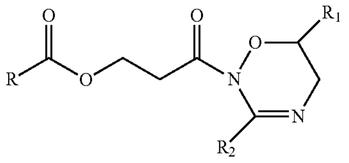

or salt, stereoisomer or solvate thereof.

In a particular embodiment, the compound in the method of the invention is the compound wherein $R_1$ and $R_2$ are the same group, or a pharmaceutically acceptable salt, stereoisomer or solvate thereof. Preferably, $R_1$ and $R_2$ are $-(CH_2)_4-CH_3$. Therefore, the compound for use in the method of the invention is selected from:

(IV)

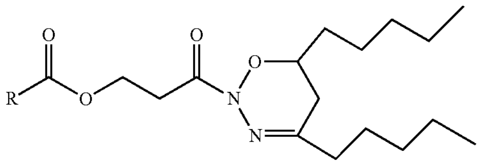

and (V)

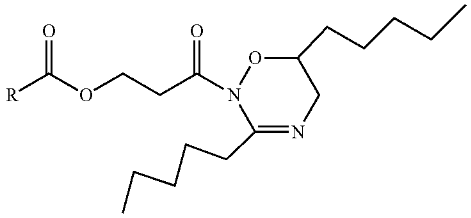

or a salt, stereoisomer or solvate thereof. In a more preferred embodiment the compound of the invention is compound (IV).

In one particular embodiment the invention refers to the compound according to the invention wherein R is a methyl group or $-(CH_2)_2-COOH$, or a salt, stereoisomer or solvate thereof. Therefore, the compound of the invention is selected from:

(IIa)

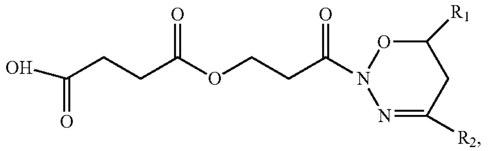

(IIIa)

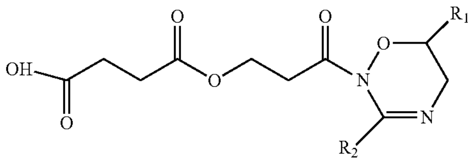

-continued (IIb)

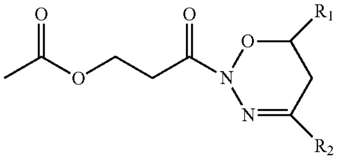

and (IIIb)

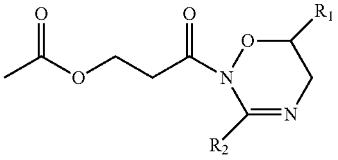

In a more preferred embodiment R is a methyl group, and $R_1$ and $R_2$ are $-(CH_2)_4-CH_3$. Therefore, the compound of the invention is selected from:

(VI)

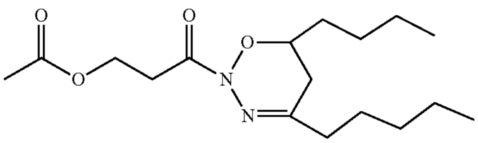

and (VII)

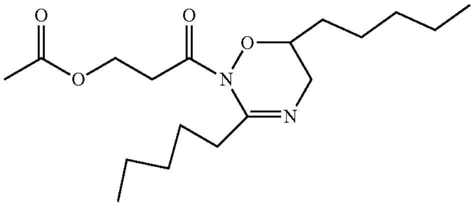

In another preferred embodiment R is $-(CH_2)_2-COOH$ and $R_1$ and $R_2$ are $-(CH_2)_4-CH_3$. Therefore the compound of the invention is (VIII)

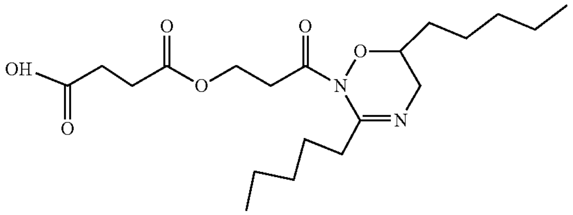

In another preferred embodiment, the compound for use in the method of the invention is (IX)

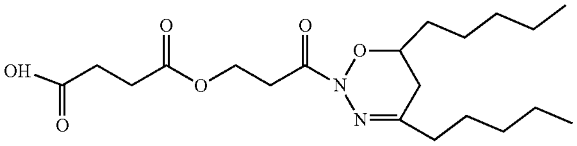

Compounds IX and VI are referred in the context of the present invention as DOXA-1 and DOXA-2 respectively.

In a more preferred embodiment the compound is

DOXA-1

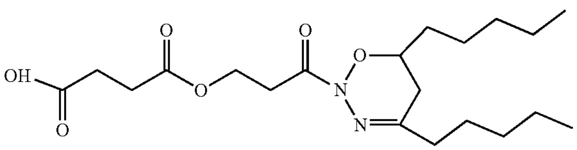

In another preferred embodiment, the compound for use in the method of the invention is

DOXA-2

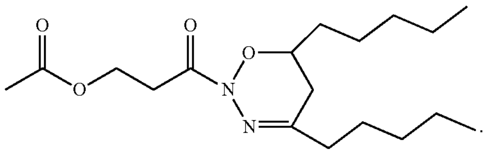

The term "food" relates preferably to fruits and vegetables.

"Enzymatic browning" is the result of PPO-catalyzed oxidation of mono- and diphenols to o-quinones which polymerize spontaneously to form dark-colored, high molecular weight polymers, leading to the characteristic browning or formation of dark spots. By enzymes is meant proteins which catalyze chemical reactions. In preferred embodiment of the method of the invention, the browning is caused by tyrosinase.

Tyrosinase (EC 1.14.18.1) is a multifunctional copper-containing enzyme, in which copper is bound by 6 or 7 histidine residues and a single cysteine residue. This enzyme possesses both monophenolase activity anddiphenolase activity. It is involved in the biosynthesis of melanin and catalyzes the ortho-hydroxylation of tyrosine (monophenol) to 3,4-dihydroxyphenylalanine or DOPA (o-diphenol), and the oxidation of DOPA to dopaquinone (o-quinone).

By "inhibition of enzymatic browning", as used herein is meant any significant slowing of the rate of browning up to and including preventing of browning. The inhibition may be at least 10%, 15%, 20%, 25%, 30%, 35%, 40%, 45%, 50%, 55% or at least 60% compared to the browning in the absence of the application of the compound of formula (I).

Inhibition of enzymatic browning may be determined by methods including, but not limited to, visual inspection, spectrophotometric quantitation, taste, smell, etc. of the food or beverage. Additionally, inhibition may be measure by detecting reduction in tyrosinase activity, by any method known in the art, such as the methods used in the examples.

The form of treatment will depend upon the food or beverage being treated, and the results sought, and can include e.g., dipping, spraying, dusting, sprinkling, immersing, mixing and/or soaking. The compounds can be added to an aqueous diluent, for example, water, salt water or buffer, and applied to the food, or can be added neat, e.g., to fruit juice. The amount needed will depend upon the susceptibility of the food or beverage to browning, the condition of the food and the storage conditions. The amount sufficient to prevent or inhibit browning can be determined empirically by one skilled in the food art.

The contact between the inhibitor compound and the food or beverage may be partial or complete, and may be for any period of time which is sufficient to inhibit non-enzymatic browning.

All the terms and embodiments previously described are equally applicable to this aspect of the invention.

The invention will be described by way of the following examples which are to be considered as merely illustrative and not limitative of the scope of the invention.

EXAMPLES

Materials and Methods

Compounds

DOXA-1 Doxadiazine-1 in DMSO 100 nM-0,195 nM

DOXA-2 Doxadiazine-2 in DMSO 100 nM-0,195 nM

DOXA-1

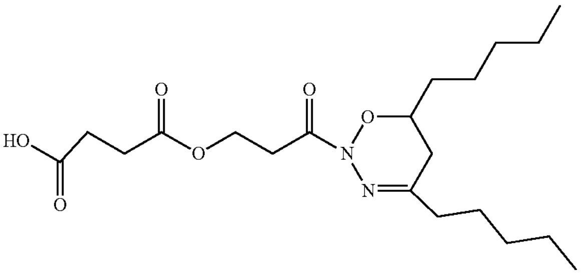

4-(3-(4,6-dipentyl-5,6-dihydro-2H-1,2,3-oxadiazin-2-yl)-3-oxopropoxy)-4-oxobutanoic acid

DOXA-2

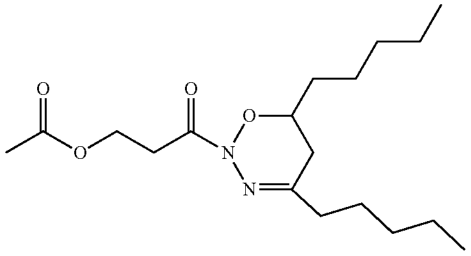

3-(4,6-dipentyl-5,6-dihydro-2H-1,2,3-oxadiazin-2-yl)-3-oxopropyl acetate

The compounds DOXA-1 and DOXA-2 can be obtained by the methods as disclosed in WO2018/197523.

Cell Cultures

The cell lines THP-1 (FiHM-IMDEA-USPCEU), NIH/3T3 (fibroblasts), B16-F10 (melanoma), maintained in supplemented DMEM medium containing 10% FBS and 1% antibiotics penicillin/streptomycin (DMEM complete medium) at 37° C. in a humidified atmosphere of 5% $CO_2$.

Cytotoxic activity assays. THP-1 cell was seeded in 96-well plates at a density of $5\times10^4$ cells/well and NIH/3T3 cells were seeded in 96-well plates at a density of $5\times10^3$ cells/well both incubated overnight at 37° C. in a humidified atmosphere of 5% $CO_2$. Subsequently, cells were treated with test compounds at the indicated concentrations and DMSO as control for 24 h. The test compounds were dissolved in DMSO (stock solution) and diluted with medium to a final DMSO concentration of 0.2%. MTT solution (50 μL, 7 mg/mL in PBS) was added to each well and plates were incubated for an additional 2 h. Next, the medium was removed and 100 μL of DMSO was added to each well to dissolve the formazan crystals that formed. The absorbance was measured at 590 nm using a spectrophotometric ELISA plate reader (SpectraMax® i3, Molecular Devices, CA, USA). Samples were considered nontoxic for the THP-1 and NIH/3T3 cell line when cell viability was ≥90%.

Total antioxidant activity assay. The DPPH assay measures hydrogen atom (or one electron) donating activity and hence provides a measure of free-radical scavenging antioxidant activity. DPPH (1,1-Diphenyl-2-picrylhydrazine) is a purple coloured stable free radical that is reduced to the yellow-coloured diphenylpicrylhydrazine. In a volume of 1 mL of methanol the test samples are mixed with DPPH 0.125 mM. Trolox (200 μM) is included as a positive control. After 30 min of incubation at room temperature in the dark the absorbance measurements are read at 517 nm using Thermo Scientific Genesys 10 uv scanning spectrophotometer. Lower absorbance of the reaction mixtures indicated higher free radical-scavenging activity. DPPH radical-scavenging activity is calculated according to the following formula:

$$\%\ \text{Antioxidant activity}=[(A_C-A_S)/A_C]\times 100$$

Where Ac (control) is the absorbance of the control reaction (DPPH) and As (sample) is the absorbance of DPPH and sample.

Cellular antioxidant activity assays. The intracellular accumulation of ROS is detected by fluorimetry using 2',7'-dihydrofluorescein-diacetate (DCFH-DA). The THP-1 cell ($1\times10^5$ cells/well) are cultured in a 96-well black plate in DMEM supplemented with 10% FBS; culture medium is renewed when the cells reached 80% confluence. For inhibition, the cells are pre-incubated with the test substances for 30 min and treated with 0.4 mM Terc-butyl-hydroperoxide (TBHP). After 3 h the cells are incubated with 10 μM DCFH-DA in the culture medium at 37° C. for 30 min.

The acetate groups on DCFH-DA are removed by an intracellular esterase, trapping the probe inside the THP-1 cell. Then, the cells are washed with PBS at 37° C. and the production of ROS measured by changes in fluorescence due to the intracellular accumulation of DCF caused by the oxidation of DCFH. Intracellular ROS, as indicated by DCF fluorescence is detected using the Incucyte FLR software; the data are analyzed by the total green object integrated intensity (GCU×$\mu m^2$×well) of the imaging system IncuCyte HD (Essen BioScience).

TNF-α activity assays. The protein expression levels of TNF-α were measured by using an enzyme-linked immunosorbent assay (ELISA) kit according to the manufacturer's instructions (Diaclone). Absorbance was read at 450 nm on a spectrophotometric ELISA plate reader (Anthos 2020, Version 2.0.5, Biochrom Ltd., UK). The percentage of TNF-α inhibition was calculated from the ratio between the observed TNF-α amount secreted by treated cells (nM) and the baseline secretion of TNF-α (nM). Dexamethasone (Sigma-Aldrich; 50-02-2), was used as positive control (0.01 μM). Results were normalized to the solvent control DMSO (0.1%).

NF-ηB activity assays. The NIH/3T3-KBF-Luc cells has been stably transfected with the plasmid KBF-Luc plasmid, which contains three copies of NF-ηB binding site (from major histocompatibility complex promoter), fused to a minimal simian virus 40 promoter driving the luciferase gene. Cells ($1\times10^4$ for NIH/3T3-KBF-Luc) are seeded the day before the assay on 96-well plate. Then the cells are treated with the test substances for 15 min and then stimulated with 30 ng/mL TNF-α. After 6 h, the cells are washed twice with PBS and lysed in 50 μL lysis buffer containing 25 mM Tris-phosphate (pH 7.8), 8 mM $MgCl_2$, 1 mM DTT, 1% Triton X-100, and 7% glycerol during 15 min at RT in a horizontal shaker. Luciferase activity is measured using a GloMax 96 microplate luminometer (Promega) following the instructions of the luciferase assay kit (Promega, Madison, WI, USA). The RLU is calculated and the results are expressed as percentage of inhibition of NF-ηB activity induced by TNF-α (100% activation). The experiments for each concentration of the test items will be done in triplicate wells.

STAT3 activity assay. The HeLa-STAT3-luc cells have been stably transfected with the plasmid 4×M67 pTATA TK-Luc. Cells ($15\times10^3$ cells/mL) are seeded 96-well plate the day before the assay. Then the cells are treated with the compound for 15 min and then stimulated with IFN-γ 25 IU/mL. After 6 h, the cells are washed twice with PBS and lysed in 50 μL lysis buffer containing 25 mM Tris-phosphate (pH 7.8), 8 mM $MgCl_2$, 1 mM DTT, 1% Triton X-100, and 7% glycerol during 15 min at RT in a horizontal shaker. Luciferase activity was measured using GloMax 96 microplate luminometer (Promega) following the instructions of the luciferase assay kit (Promega, Madison, WI, USA). The RLU is calculated and the results are expressed as percentage of inhibition of STAT3 activity induced by IFN-γ (100% activation). The experiments for each concentration of the test items will be done in triplicate wells.

HIF-1α activity assay. The NIH/3T3-EPO-luc cells have been stably transfected with the plasmid Epo-Luc plasmid. The EPO-Hypoxia Response Element (HRE)-luciferase reporter plasmid contains three copies of the HRE consensus sequence from the promoter of the erythropoietin gene in the pGL3 vector. Cells ($1\times10^4$ for NIH/3T3-EPO-luc) are seeded the day before the assay. The next day, the cells are stimulated either with the compound or Desferrioxamine (DFX) 150 μM as a positive control. After 6 hours of stimulation the cells are lysed in 25 mM Tris-phosphate pH 7.8, 8 mM $MgCl_2$, 1 mM DTT, 1% Triton X-100, and 7% glycerol during 15 min at RT in a horizontal shaker. Luciferase activity is measured using a GloMax 96 microplate luminometer (Promega) following the instructions of the luciferase assay kit (Promega, Madison, WI, USA). The RLU is calculated and the results are expressed as percentage of inhibition induction/inhibition of EPO-luc activity. The experimentsfor each concentration of the test items will be done in triplicate wells.

Tyrosinase activity assay. To measure the tyrosinase activity of the cells, the B16-F10 cells treated for 3 days with several doses of the compound is lysed by incubation at 4° C. for 30 min in lysis buffer (20 mM sodium phosphate, pH 6.8, 1% Triton X-100, 1 mM PMSF, 1 mM EDTA) containing protease inhibitors cocktail. The lysates are centrifuged at 15,000× g for 10 min to obtain the supernatant as the source of tyrosinase. The reaction mixture contained 20 mM phosphate buffer, pH 6.8, 1.25 mM L-DOPA (Sigma-Aldrich). After incubation at 37° C. for 2 h, dopachrome formation is monitored by measuring absorbance at a wavelength of 475 nm in a microplatereader (TECAN). Kojic acid 2 mM is used as a positive control.

Results

Example 1—Cytotoxicity Activity Assays

To analyse the cytotoxic activities of the test compound, THP-1 cells were incubated with DOXA-1 and DOXA-2 for 48 h and cytotoxicity was measured by fluorescence microscopy using an Incuyte microscope. All samples showed no cytotoxicity against THP-1 cell at the tested concentrations (FIG. 1).

Example 2—Total Antioxidant Activity Assay

Figure 2:
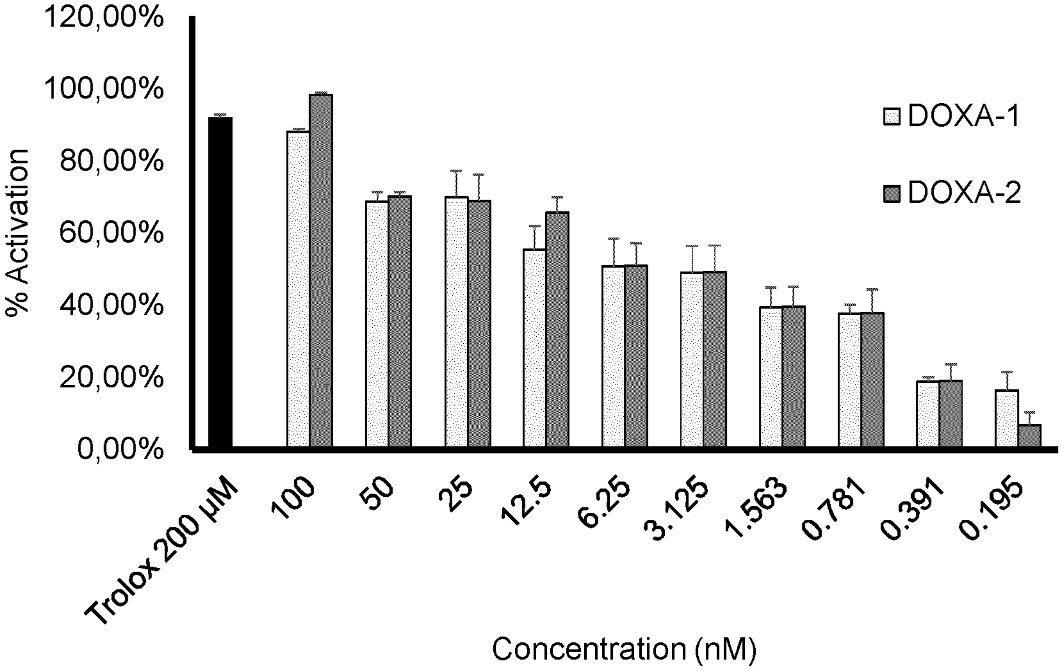
FIG. 2. Antioxidant activity of compound. The percentage of antioxidant activity of each extract was assessed by DPPH free radical assay and compared to the standard Trolox (92.08% of antioxidant activity).

DOXA-1 and DOXA-2 showed an antioxidant activity with $IC_{50}$ of 4.608 nM and 3.364 nM respectively, in a cell-free assay (DPPH) (FIG. 2).

Example 3—Cellular Antioxidant Activity Assays

Figure 3:
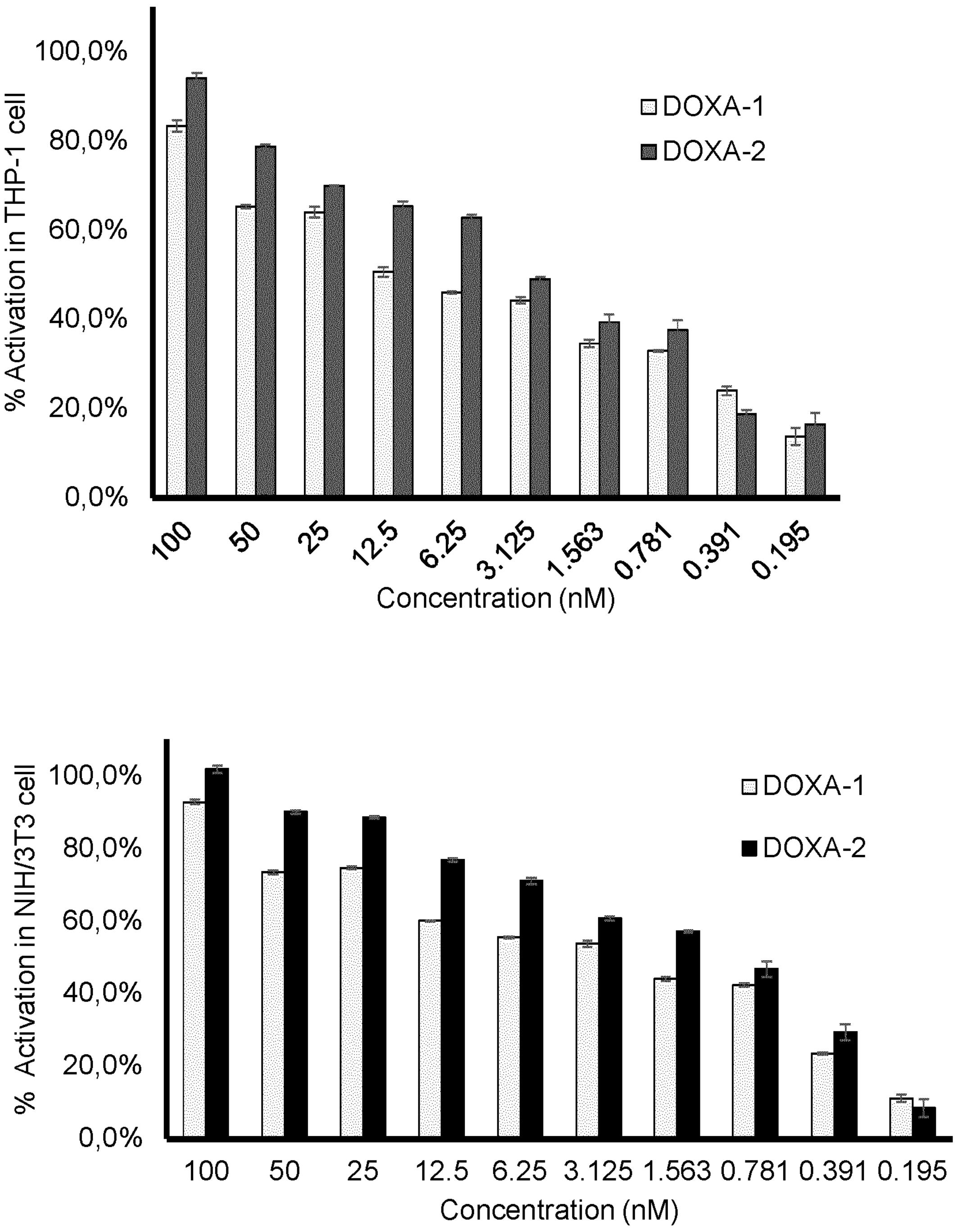
FIG. 3. Inhibition of TBHP-induced ROS production in THP-1 and NIH-3T3 cells. ROS production was evaluated by fluorescent probe DCFH-DA assay.

DOXA-1 and DOXA-2 showed antioxidant activity in THP-1 cell with $IC_{50}$ of 8.151 nM and 3.441 nM. Also, showed antioxidant activity in NIH/3T3 cell with $IC_{50}$ of 3,329 nM, 2.228 nM and 1.12 nM. In both cases the intracellular levels of ROS induced by TBHP are reduced (FIG. 3).

Example 4—TNF-α Activity Assays

Figure 4:
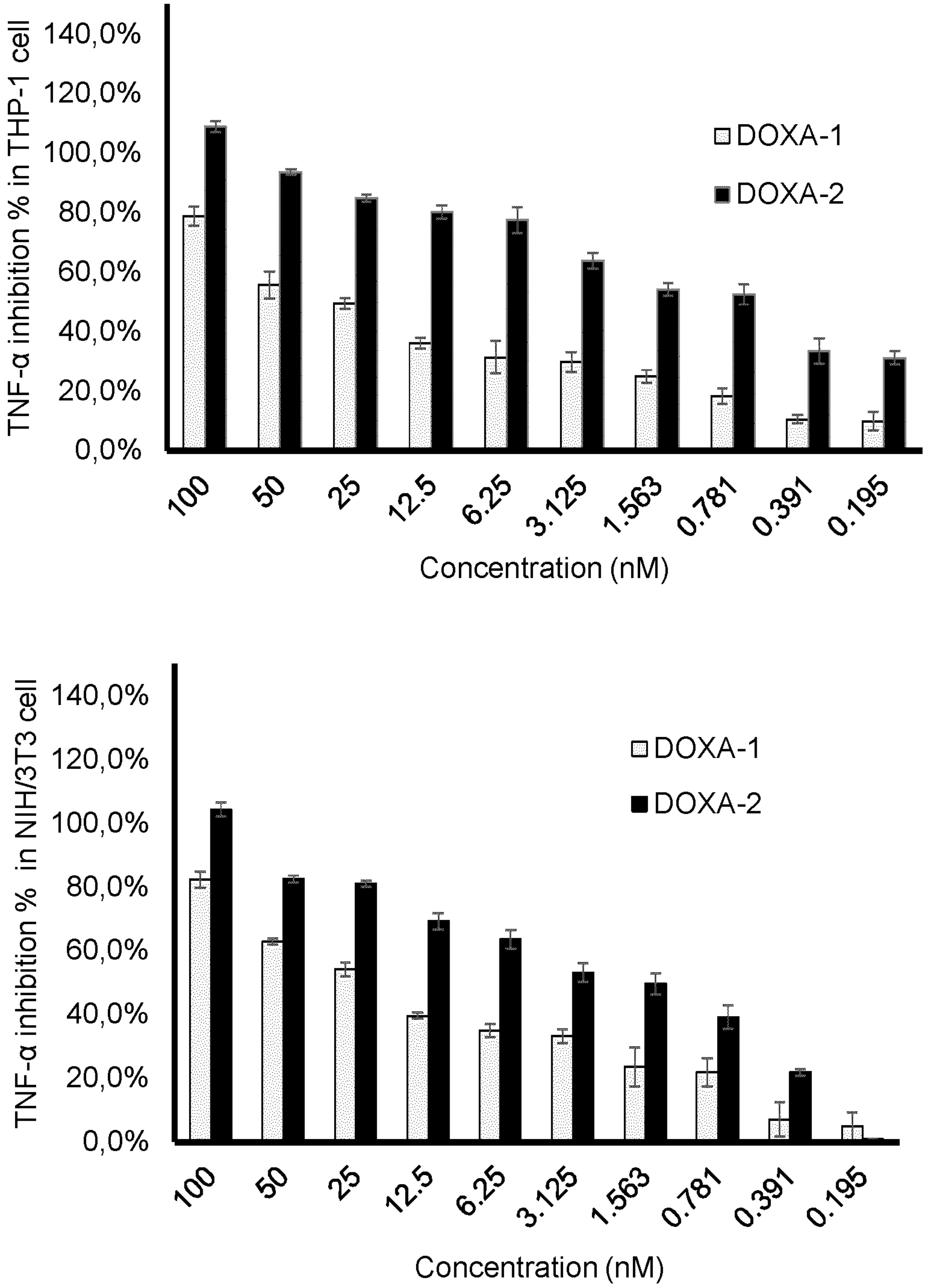
FIG. 4. Inhibition of TNF-α production in THP-1 and NIH/3T3 cells.

DOXA-1 and DOXA-2 showed inhibition of TNF-α production in THP-1 cell with $IC_{50}$ of 32.53 nM and 3.469 nM. Also, showed inhibition of TNF-α production in NIH/3T3 cell with $IC_{50}$ of 17.39 nM and 1.58 nM, respectively (FIG. 4).

Example 5—NF-ηB Activity Assays

Figure 5:
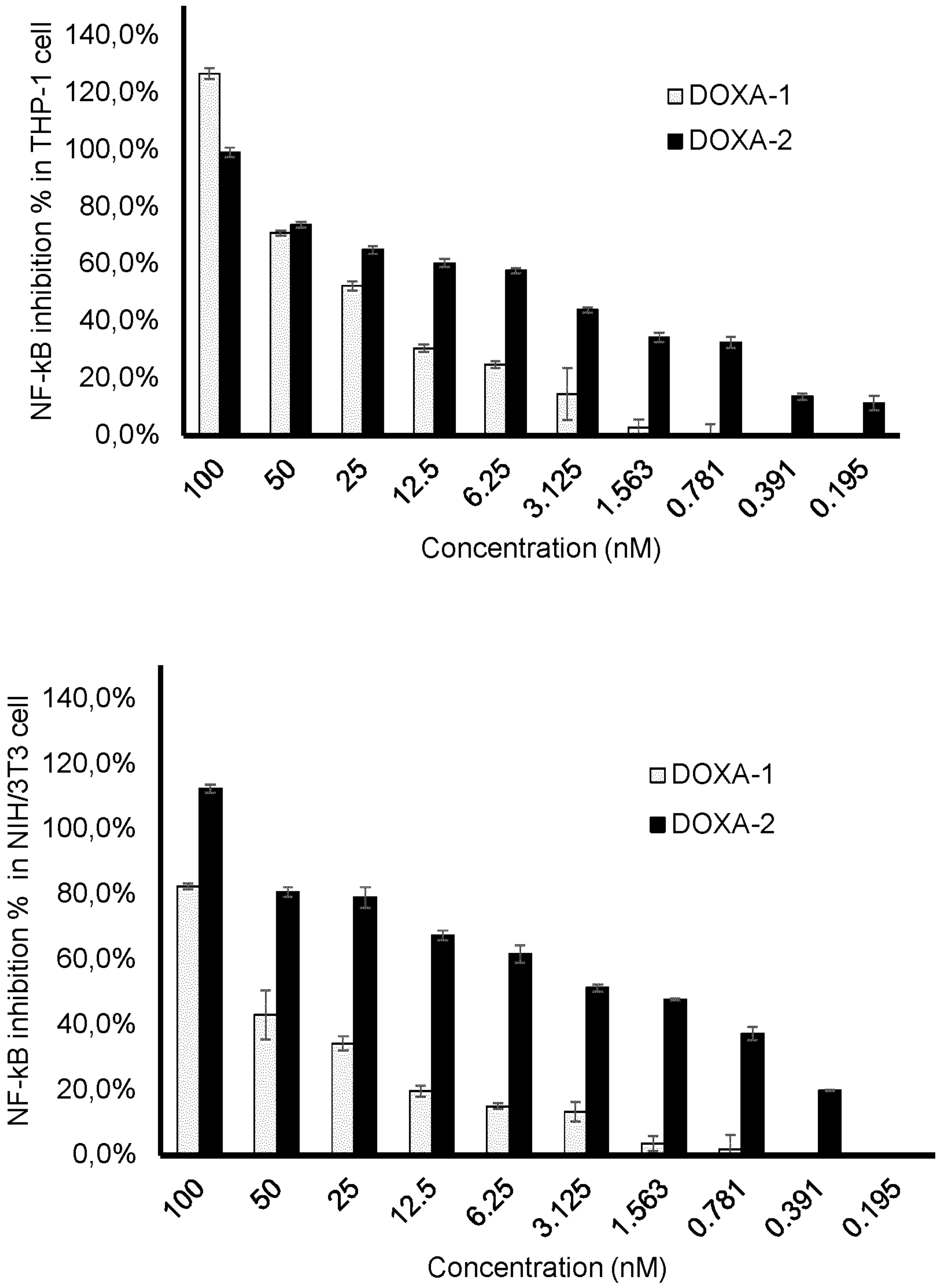
FIG. 5. Inhibition of NF-ηB production in THP-1 and NIH/3T3 cells.

DOXA-1 and DOXA-2 showed inhibition of NF-ηB production in THP-1 cell with $IC_{50}$ of 63.62 nM and 5.182 nM. Also, showed inhibition of NF-ηB production in NIH/3T3 cell with $IC_{50}$ of 67.67 nM and 2.414 nM (FIG. 5).

Example 6—STAT3 Activity Assay

Figure 6:
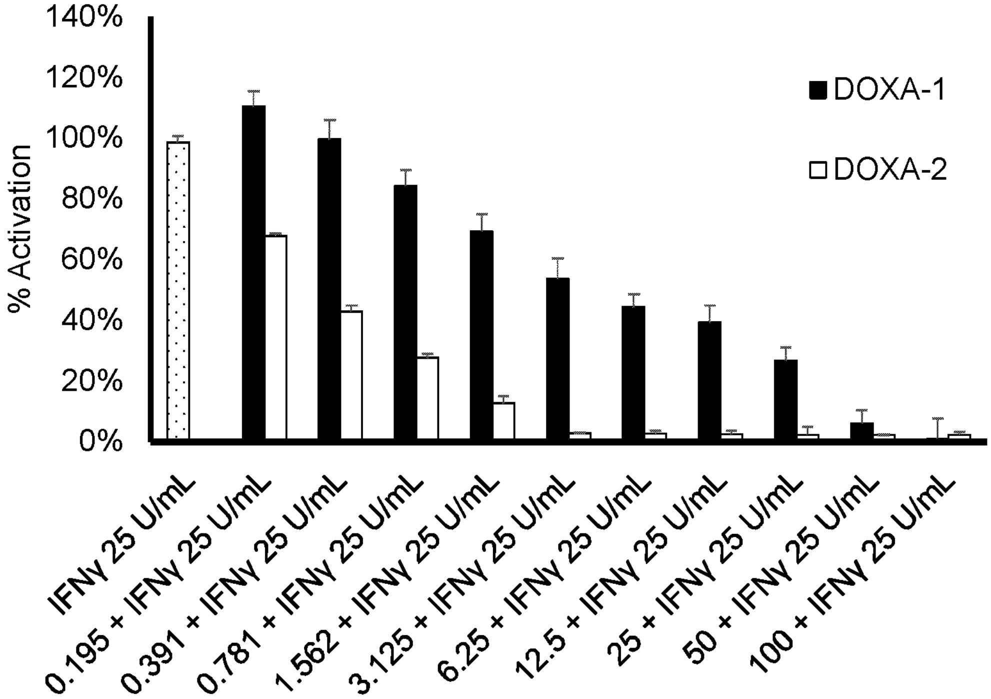
FIG. 6. DOXA-1 and DOXA-2 inhibits IFNγ-induced STAT3 activation. HeLa-STAT3-Luc cells ($15\times10^3$ cells/mL) were preincubated with increasing concentrations of the compound and treated with IFNγ (25 U/mL) for 6 h. Luciferase activity was measured in the cell lysates with the luciferase assay kit (Promega, USA) and using a GloMax 96 microplate luminometer FIG. 7. Inhibitions the HIF-1α pathway. NIH/3T3-EPO-Luc cells ($10\times10^4$ cells/mL) were preincubated with increasing concentrations of the compound or the hypoximimetic (Desferrioxamine) DFX for 6 h. Luciferase activity was measured in the cell lysates and results are represented as the percentage of inhibition considering 100% the value of DFX-induced HIF-1α pathway activation.

DOXA-1 and DOXA-2 inhibited IFNγ-induced STAT3 activation with $IC_{50}$ of 3.088 nM and 0.1396 nM respectively (FIG. 6).

Example 7—HIF-1α Activity Assay

Figure 7:
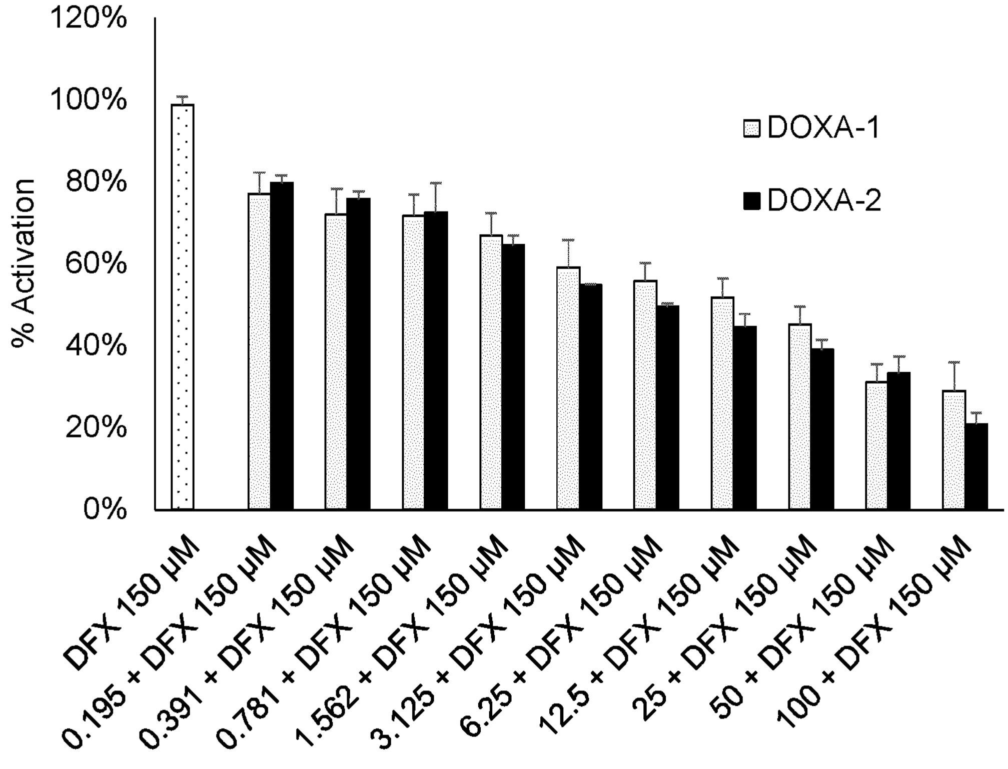

DOXA-1 and DOXA-2 was found to inhibit DFX-induced activation of EPO-Luc as a surrogated marker of HIF-1α stabilization with $IC_{50}$ of 12.42 nM and 5.07 nM respectively in NIH/3T3-EPO-Luc (FIG. 7).

Example 8—Tyrosinase Activity Assay

Figure 8:
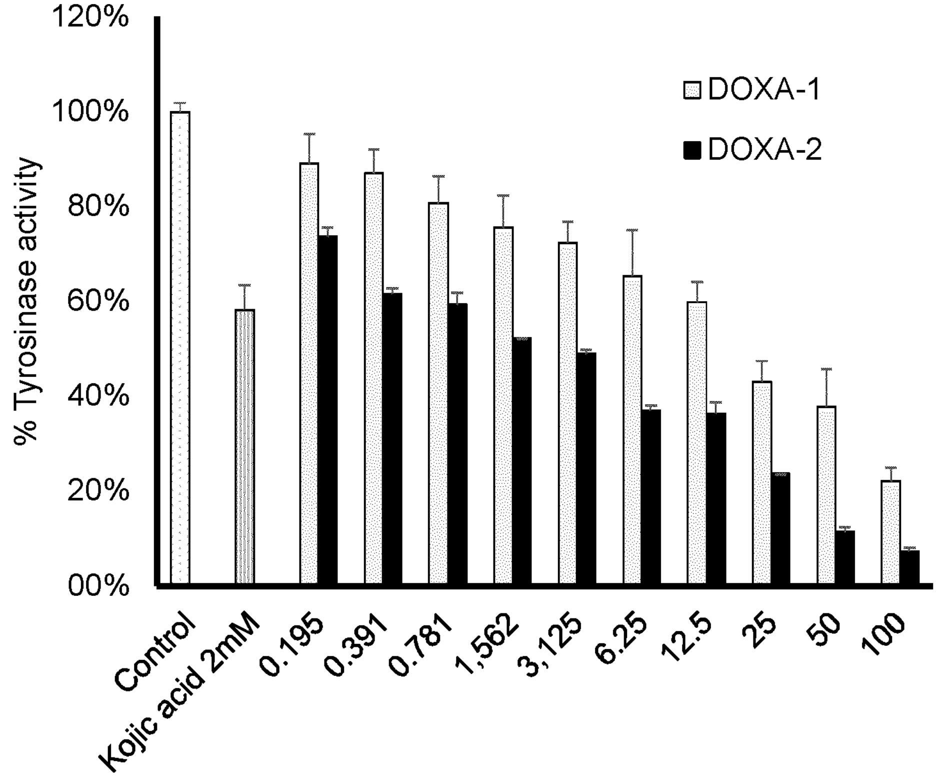
FIG. 8. Effect of DOXA-1 and DOXA-2 on tyrosinase activity in B16-F10 melanoma cells. Tyrosinase activity assessment was performed as described in Methods. Briefly, cells were treated with the doses indicated of test substances or Kojic Acid as a positive control for 72 h. To determine the tyrosinase activity cells were lysed and the protein extracts were incubated with L-DOPA (a precursor of melanin) at 37°

DOXA-1 and DOXA-2 inhibit melanin synthesis with $IC_{50}$ of 18.00 nM and 8.64 nM respectively in B16-F10 cells. (FIG. 8).

The invention claimed is:

1. A method of treatment, not including a prophylactic nor preventative treatment, of a pathology associated with proinflammatory conditions, a disease associated with oxidative stress or production of reactive oxygen species or a skin pigmentation disorder in a subject comprising: administering to said subject of a compound of formula (I) or a pharmaceutically acceptable salt, stereoisomer or solvate thereof,

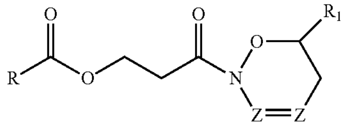

(I)

wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)O—$CH_2$—, amine di-substituted with independently selected $C_{1-6}$ alkyl groups, b) phenyl optionally substituted with one or more groups independently selected from $C_{1-8}$ alkyl, $C_{2-8}$ alkenyl, halogen, phenyl, $C_{1-6}$ alkoxy, amine di-substituted with independently selected $C_{1-6}$ alkyl groups, —NHC(O)$R_3$—, —C(O)NH—$R_3$, —OC(O)$R_3$, and —C(O)$OR_3$—, wherein $R_3$ is $C_{1-6}$ alkyl, c) a 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl phenyl as defined in b)

5-6 membered aromatic ring group halogen, ($C_{1-6}$alkyl)$OCH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)$OR_3$—, wherein $R_3$ is $C_{1-6}$ alkyl d) a bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from $C_{1-8}$ alkyl, linear or branched $C_{2-8}$ alkenyl, $C_{5-6}$ cycloalkyl phenyl as defined in b)

5-6 membered aromatic ring group halogen, ($C_{1-6}$alkyl)$OCH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)$OR_3$—, wherein $R_3$ is $C_{1-6}$ alkyl, and e) —CH($R_4$)—CH($R_5$) COOH, wherein $R_4$ is selected from H, $NH_2$, OH and $CH_2COOH$, and wherein $R_3$ is selected from H, $NH_2$, OH and $CH_2COOH$.

2. The method according to claim 1, wherein the compound of formula (I) $R_1$ and $R_2$ are the same group.

3. The method according to claim 1, wherein the compound of formula (I) $R_1$ and $R_2$ are —$(CH2)_4$—$CH_3$.

4. The method according to claim 3, wherein the compound of formula (I) is the compound of formula

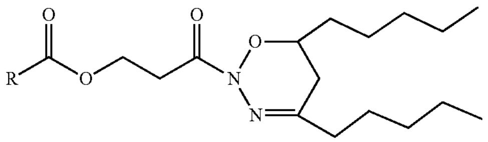

or

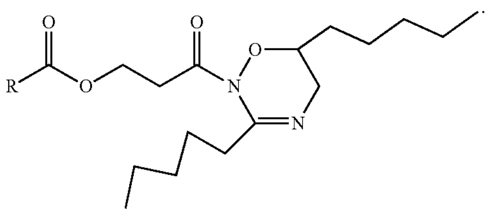

5. The method according to claim 1, wherein the compound of formula (I) R is a methyl group or —(CH2)$_2$—COOH, or a pharmaceutically acceptable salt, stereoisomer or solvate thereof.

6. The method according to claim 1, wherein the disease related to a proinflammatory condition is a skin disease selected from the group consisting of psoriasis, eczema, vitiligo, impetigo, acne, rosacea, urticaria, melasma and alopecia.

7. The method according to claim 1, wherein the disease associate with oxidative stress or production of reactive oxygen species is selected from the group consisting of cerebrovascular diseases, cardiovascular diseases, respiratory diseases, musculoskeletal diseases, gastrointestinal diseases, age-related immune deficiency and premature aging disorders, ear diseases, eye diseases, drug-induced toxicity and wherein the skin pigmentation disorder is selected from the group consisting of melasma, drug-induced hyperpigmentation, acanthosis nigricans, lentigines, Addison's disease and hemochromatosis.

8. A cosmetic method for treating thin and dry skin, fine wrinkles, decreased elasticity, aberrant pigmentation, hair graying and hair loss, irradiated skin damage and for skin whitening in a subject comprising:

administering a compound of formula (I) or a cosmetically acceptable salt, stereoisomer or solvate thereof, (I)

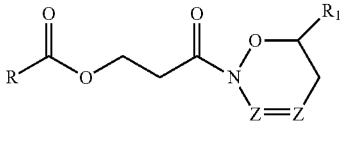

wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)O—$CH_2$—, amine di-substituted with independently selected $C_{1-6}$ alkyl groups, b) phenyl optionally substituted with one or more groups independently selected from $C_{1-8}$ alkyl, $C_{2-8}$ alkenyl, halogen, phenyl, $C_{1-6}$ alkoxy, amine di-substituted with independently selected $C_{1-6}$ alkyl groups, —NHC(O)$R_3$—, —C(O)NH—$R_3$, —OC(O)$R_3$, and —C(O)O$R_3$—, wherein $R_3$ is $C_{1-6}$ alkyl, c) a 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl phenyl as defined in b)

5-6 membered aromatic ring group halogen, ($C_{1-6}$alkyl)O$CH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)O$R_3$—, wherein $R_3$ is $C_{1-6}$ alkyl d) a bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from $C_{1-8}$ alkyl, linear or branched $C_{2-8}$ alkenyl, $C_{5-6}$ cycloalkyl phenyl as defined in b)

5-6 membered aromatic ring group halogen, ($C_{1-6}$alkyl)O$CH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)O$R_3$—, wherein $R_3$ is $C_{1-6}$ alkyl, and e) —CH($R_4$)—CH($R_5$)COOH, wherein $R_4$ is selected from H, $NH_2$, OH and $CH_2COOH$, and wherein $R_5$ is selected from H, $NH_2$, OH and $CH_2COOH$, to a subject in need thereof.

9. The cosmetic method according to claim 8, wherein $R_1$ and $R_2$ of the compound of formula (I) are the same group.

10. The cosmetic method according to claim 9, wherein the compound of formula (I) is the compound of formula

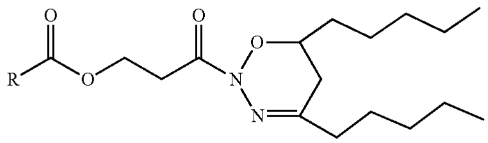

or

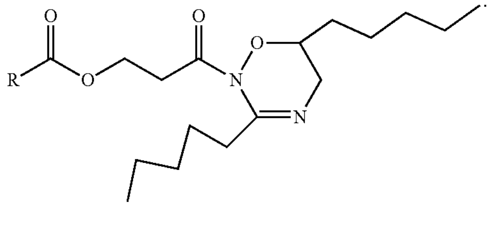

11. The cosmetic method according to claim 8, wherein R of the compound of formula (I) is a methyl group or —$(CH_2)_2$—COOH, or a cosmetically acceptable salt, stereoisomer or solvate thereof.

12. A method of inhibition of enzymatic browning in food or beverage comprising:

contacting said food or beverage with a compound of formula (I) or a salt, stereoisomer or solvate thereof

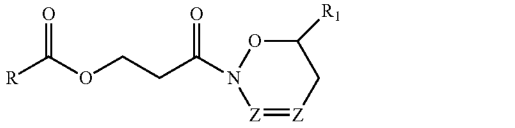

(I)

wherein one Z is N and the other is —C—$R_2$; and $R_2$ and $R_1$ are independently selected from the group consisting of H, alkyl and aryl, and wherein R is selected from a group consisting of a) a linear or branched $C_{1-8}$ alkyl, a linear or branched $C_{2-8}$ alkenyl, di-halo methyl, tri-halo methyl, $C_{3-6}$ cycloalkyl, ($C_{1-6}$ alkyl)O—$CH_2$—, amine di-substituted with independently selected $C_{1-6}$ alkyl groups, b) phenyl optionally substituted with one or more groups independently selected from $C_{1-8}$ alkyl, $C_{2-8}$ alkenyl, halogen, phenyl, $C_{1-6}$ alkoxy, amine di-substituted with independently selected $C_{1-6}$ alkyl groups, —NHC(O)$R_3$—, —C(O)NH—$R_3$, —OC(O)$R_3$, and —C(O)O$R_3$—, wherein $R_3$ is $C_{1-6}$ alkyl, c) a 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl phenyl as defined in b)

5-6 membered aromatic ring group halogen, ($C_{1-6}$alkyl)O$CH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)O$R_3$—, wherein $R_3$ is $C_{1-6}$ alkyl d) a bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from $C_{1-8}$ alkyl, linear or branched $C_{2-8}$ alkenyl, $C_{5-6}$ cycloalkyl phenyl as defined in b)

5-6 membered aromatic ring group halogen, ($C_{1-6}$alkyl)O$CH_2$—, $C_{1-6}$ alkoxy, amino di-substituted with $C_{1-6}$ alkyl groups, NHC(O)$R_3$—, —C(O)NH—$R_3$, —OC(O)$R_3$, and —C(O)O$R_3$—, wherein $R_3$ is $C_{1-6}$ alkyl, and e) —CH($R_4$)—CH($R_5$)COOH, wherein $R_4$ is selected from H, $NH_2$, OH and $CH_2COOH$, and wherein $R_5$ is selected from H, $NH_2$, OH and $CH_2COOH$.

13. The method according to claim 12, wherein the compound of formula (I) is

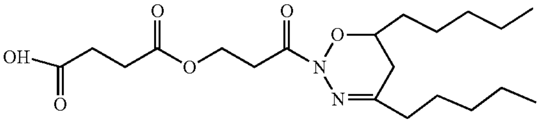

or

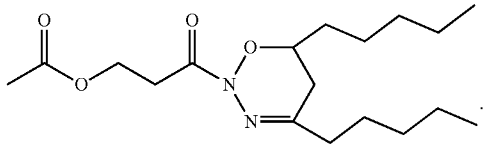

* * * * *